United States Patent
Jak

(10) Patent No.: US 10,289,008 B2
(45) Date of Patent: May 14, 2019

(54) METHODS AND APPARATUS FOR PREDICTING PERFORMANCE OF A MEASUREMENT METHOD, MEASUREMENT METHOD AND APPARATUS

(71) Applicant: ASML Netherlands B.V., Veldhoven (NL)

(72) Inventor: Martin Jacobus Johan Jak, 's-Hertogenbosch (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/834,763

(22) Filed: Dec. 7, 2017

(65) Prior Publication Data
US 2018/0203367 A1 Jul. 19, 2018

(30) Foreign Application Priority Data
Dec. 9, 2016 (EP) .................................. 16203208

(51) Int. Cl.
*G03F 7/20* (2006.01)
*G01N 21/95* (2006.01)
(Continued)

(52) U.S. Cl.
CPC ..... *G03F 7/70516* (2013.01); *G01N 21/9501* (2013.01); *G01N 21/956* (2013.01);
(Continued)

(58) Field of Classification Search
CPC .......... G01N 21/8822; G01N 21/9501; G01N 21/956; G03F 7/70483; G03F 7/705;
(Continued)

(56) References Cited

U.S. PATENT DOCUMENTS

2006/0033921 A1 2/2006 Den Boef et al.
2006/0066855 A1 3/2006 Boef et al.
(Continued)

FOREIGN PATENT DOCUMENTS

WO WO 2014/068116 A1 5/2014
WO WO 2015/185166 A1 12/2015
(Continued)

OTHER PUBLICATIONS

International Search Report and Written Opinion of the International searching Authority directed to related International Patent Application No. PCT/EP2017/079774, dated Mar. 15, 2018; 12 pages.
(Continued)

*Primary Examiner* — Colin W Kreutzer
(74) *Attorney, Agent, or Firm* — Sterne, Kessler, Goldstein & Fox P.L.L.C.

(57) ABSTRACT

An overlay measurement (OV) is based on asymmetry in a diffraction spectrum of target structures formed by a lithographic process. Stack difference between target structures can be perceived as grating imbalance (GI), and the accuracy of the overlay measurement may be degraded. A method of predicting GI sensitivity is performed using first and second images (45+, 45−) of the target structure using opposite diffraction orders. Regions (ROI) of the same images are used to measure overlay. Multiple local measurements of symmetry (S) and asymmetry (A) of intensity between the opposite diffraction orders are made, each local measurement of symmetry and asymmetry corresponding to a particular location on the target structure. Based on a statistical analysis of the local measurements of symmetry and asymmetry values, a prediction of sensitivity to grating imbalance is obtained. This can be used to select better measurement
(Continued)

recipes, and/or to correct errors caused by grating imbalance.

23 Claims, 12 Drawing Sheets

(51) Int. Cl.
    *G01N 21/956*     (2006.01)
    *G03F 9/00*     (2006.01)

(52) U.S. Cl.
    CPC .......... *G03F 7/705* (2013.01); *G03F 7/70483* (2013.01); *G03F 7/70508* (2013.01); *G03F 7/70616* (2013.01); *G03F 7/70625* (2013.01); *G03F 7/70633* (2013.01); *G03F 7/70683* (2013.01); *G03F 9/7088* (2013.01)

(58) Field of Classification Search
    CPC ............. G03F 7/70508; G03F 7/70516; G03F 7/70616; G03F 7/70625; G03F 7/70633; G03F 7/70683; G03F 9/7088
    USPC ........................ 355/67, 68, 77; 356/399–401
    See application file for complete search history.

(56) References Cited

U.S. PATENT DOCUMENTS

| | | |
|---|---|---|
| 2010/0201963 A1 | 8/2010 | Cramer et al. |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2011/0102753 A1 | 5/2011 | Van De Kerkhof et al. |
| 2012/0044470 A1 | 2/2012 | Smilde et al. |
| 2012/0123581 A1 | 5/2012 | Smilde et al. |
| 2013/0258310 A1 | 10/2013 | Smilde et al. |
| 2013/0271740 A1 | 10/2013 | Quitanilha |
| 2014/0192338 A1 | 7/2014 | Den Boef |
| 2015/0346605 A1 | 12/2015 | Den Boef et al. |
| 2016/0091422 A1 | 3/2016 | Van Der Zouw |
| 2016/0291481 A1 | 10/2016 | Smilde et al. |
| 2016/0299438 A1 | 10/2016 | Mos et al. |

FOREIGN PATENT DOCUMENTS

| | | |
|---|---|---|
| WO | WO 2016/162228 A1 | 10/2016 |
| WO | WO 2016/162231 A1 | 10/2016 |

OTHER PUBLICATIONS

Taiwanese Office Action from related Taiwanese Patent Application No. 106142911 with English-language Translation Attached, dated Jan. 22, 2019; 11 pages.

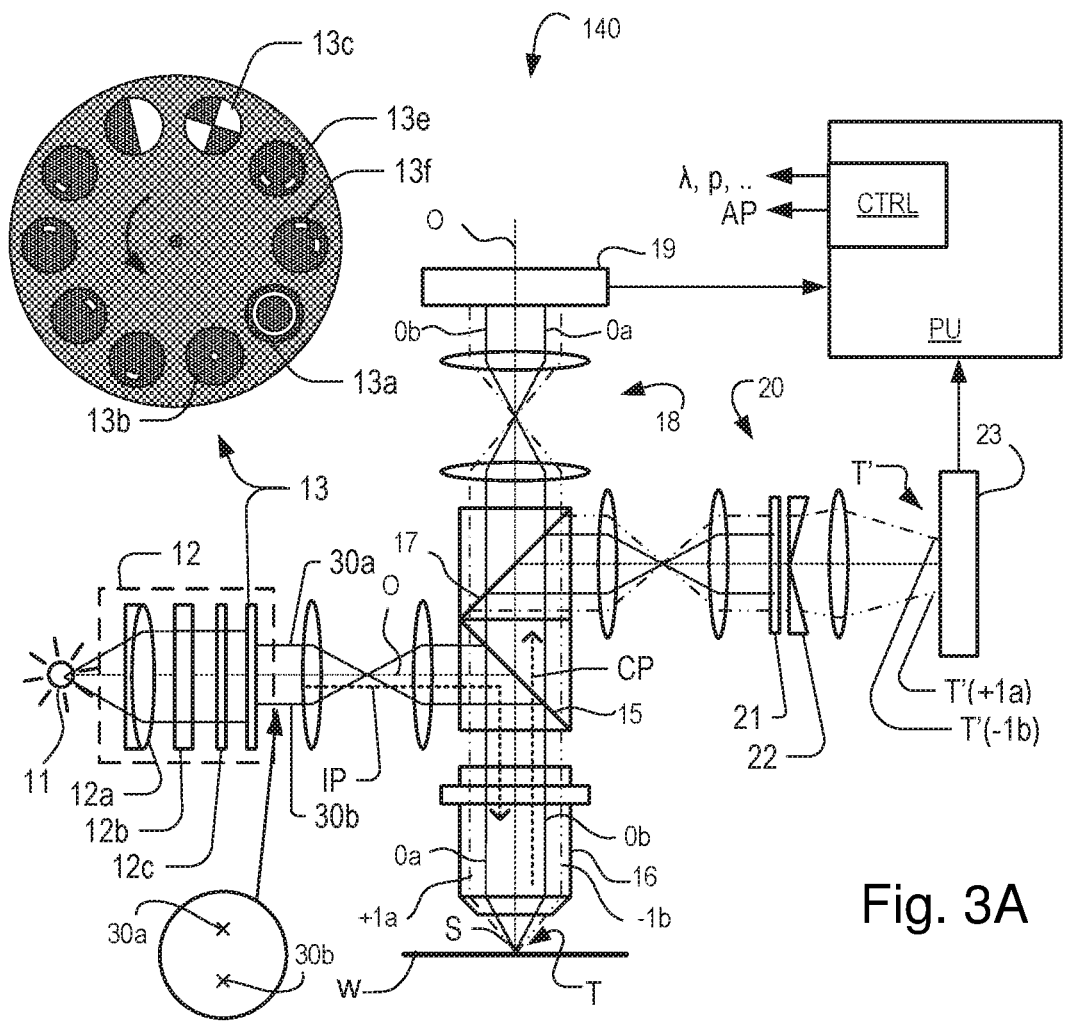
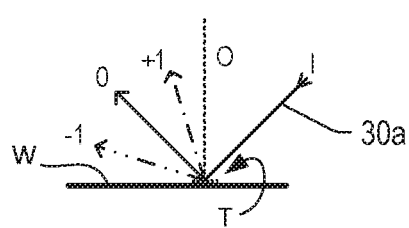
Fig. 3A
FIG. 3B

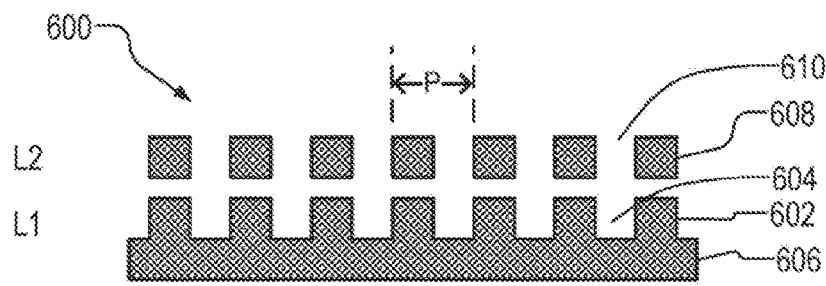
FIG. 7A
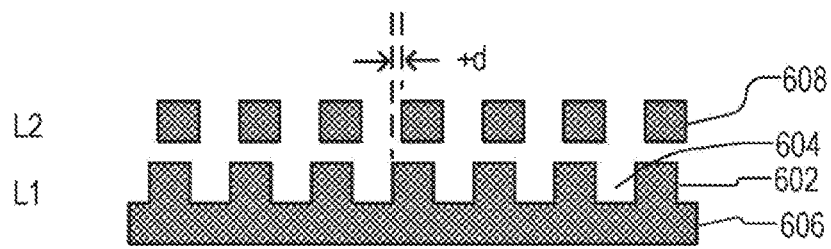
FIG. 7B
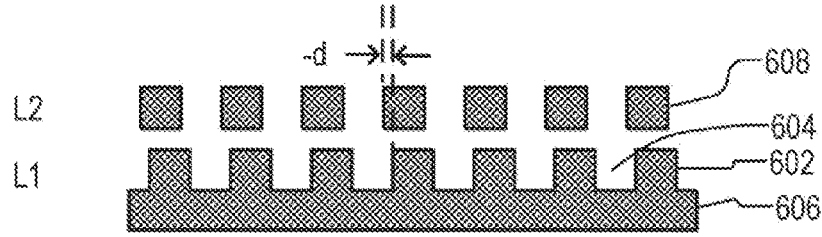
FIG. 7C
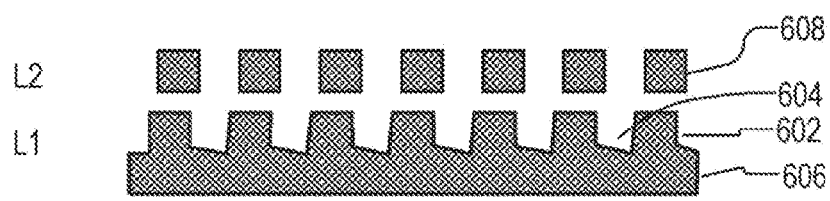
FIG. 7D

METHODS AND APPARATUS FOR PREDICTING PERFORMANCE OF A MEASUREMENT METHOD, MEASUREMENT METHOD AND APPARATUS

FIELD

The present disclosure relates to methods and apparatus for inspection (e.g., metrology) usable, for example, in the manufacture of devices by lithographic techniques and to methods of manufacturing devices using lithographic techniques.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. These target portions are commonly referred to as "fields".

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921 A1 and US2010201963 A1. The targets used by such scatterometers are relatively large, e.g., 40 μm by 40 μm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855 A1. Diffraction-based overlay metrology using dark-field imaging of the diffraction orders enables overlay measurements on smaller targets. Examples of dark field imaging metrology can be found in international patent applications US2014192338 and US2011069292 A1 which documents are hereby incorporated by reference in their entirety. Further developments of the technique have been described in published patent publications US20110027704 A, US20110043791 A, US2011102753 A1, US20120044470 A, US20120123581 A, US20130258310 A US20130271740 A and US2016091422 A1. These targets can be smaller than the illumination spot and may be surrounded by product structures on a wafer. Multiple gratings can be measured in one image, using a composite grating target. The contents of all these applications are also incorporated herein by reference.

An overlay measurement is typically obtained by measuring asymmetry of two overlay gratings, each having a different programmed (deliberate) offset or "bias". Although, the overlay measurements are fast and computationally very simple (once calibrated), they rely on an assumption that overlay (i.e., overlay error and deliberate bias) is the only cause of asymmetry in the target. Any other asymmetry in the target perturbs the overlay measurement, giving an inaccurate overlay measurement. Asymmetry in the lower or bottom periodic structure of a target is a common form of structural asymmetry. It may originate for example in substrate processing steps such as chemical-mechanical polishing (CMP), performed after the bottom periodic structure was originally formed.

When using two or more biased grating structures to obtain an overlay measurement, the known method further assumes that the two gratings are identical, apart from the bias. It has been discovered that, in addition to or alternatively to structural asymmetry in a target, a difference between adjacent periodic structures of a target or between adjacent targets may be a factor that adversely affects the accuracy of measurement, such as overlay measurement. This difference may be referred to as "stack difference", and encompasses any unintentional difference in physical configurations between periodic structures or targets. Stack difference imbalance includes, but is not limited to, a thickness difference in one or more layers of the stack between the adjacent periodic structures or targets, a refractive index difference between the adjacent periodic structures or targets, a difference in material between the adjacent periodic structures or targets, a difference in the grating CD or height of the structures of adjacent periodic structures or targets, etc. Like structural asymmetry, the stack difference may be introduced by processing steps, such as CMP, layer deposition, etc. in the patterning process.

When such structures are measured for the purposes of an overlay measurement, the stack difference may influence the measurement signals. Where asymmetry is measured through a difference between diffraction signal of opposite diffraction orders, the stack difference may cause for example a difference in the average of the diffraction signals as well. The influence of the stack difference that is represented in the measurement signals may be referred to as "grating imbalance".

SUMMARY OF THE INVENTION

The inventors have recognized that, if the sensitivity of a measurement to grating imbalance were known, it might be possible to identify one or more desired metrology target measurement recipes (e.g., a particular desired target design and/or one or more particular measurement parameters (such as measurement beam wavelength and/or polarization)). Additionally or alternatively, if the grating imbalance and the sensitivity of a measurement to grating imbalance could be known at the time of calculating a measurement such as overlay, an uncertainty measure (measurement quality measure) could be delivered along with the measurement. It may further be possible to determine an improved measurement of overlay using a determined grating imbalance and grating imbalance sensitivity.

Accordingly, the present invention seeks to provide a method of predicting performance of a measurement method, the measurement method being based on asymmetry in a diffraction spectrum of periodic features within one or more target structures formed by a lithographic process. The aim of the invention is particularly to allow prediction of the sensitivity of the measurement method to grating imbalance, and/or to allow prediction of an error attributable by grating imbalance in individual measurements. To be usable in high-volume manufacture, a method should be one that does not in itself add greatly to the overhead involved in the measurement method.

The present invention in a first aspect provides a method of predicting performance of a measurement method, the measurement method being based on asymmetry in a diffraction spectrum of periodic features within one or more target structures formed by a lithographic process, the method of predicting performance including the steps:

(a) forming first and second images of the target structure using symmetrically opposite portions of said diffraction spectrum of radiation diffracted by the target structure;

(b) from said first and second images, deriving multiple local measurements of symmetry and asymmetry of intensity between opposite portions of the diffraction spectrum, each local measurement of symmetry and asymmetry corresponding to a particular location on the target structure; and (c) based on a statistical analysis of the local measurements of symmetry and asymmetry values, determining a prediction of performance for the measurement method.

The prediction of performance obtained in this way can be for example a measure of sensitivity to grating imbalance.

Embodiments of the method may further include a step (d) of performing the measurement method to obtain a measurement of a property of the same or a similar target structure.

In some embodiments, the measurement of the property of the target structure may be reported together with a prediction of performance of the measurement method.

In some embodiments, the step (d) further comprises applying a correction to the measurement of the property, using the prediction of performance obtained in step (c).

The invention further provides a metrology apparatus for measuring a parameter of a lithographic process, the metrology apparatus being operable to perform the method according to the first aspect of the invention, as set forth above.

The invention further provides a non-transitory computer program product comprising machine-readable instructions for causing a processor to cause performance of the method according to the first aspect of the invention, as set forth above.

The invention further provides a system comprising an inspection apparatus configured to provide a beam of radiation on a target structure, and to detect radiation diffracted by the targets to determine a parameter of a patterning process, in combination with the non-transitory computer program according to the invention as set forth above. The system may further comprise a lithographic apparatus comprising a support structure configured to hold a patterning device to modulate a radiation beam and a projection optical system arranged to project the modulated radiation beam onto a radiation-sensitive substrate.

Further features and advantages, as well as the structure and operation of various embodiments, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which:

FIGS. 3A-3B illustrate schematically FIG. 3A an inspection apparatus adapted to perform angle-resolved scatterometry and dark-field imaging inspection methods in accordance with some embodiments of the invention and FIG. 3B an enlarged detail of the diffraction of incident radiation by a target grating in the apparatus of FIG. 3A;

FIG. 7A, FIG. 7B and FIG. 7C respectively show schematic cross-sections of overlay periodic structures having different overlay values in the region of zero;

FIG. 7D is a schematic cross-section of an overlay periodic structure having structural asymmetry in a bottom periodic structure due to processing effects;

Figure 5:
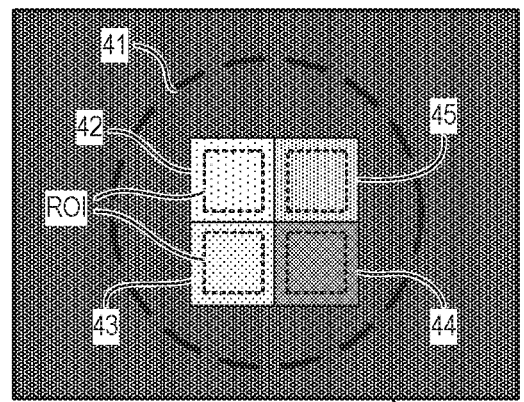
FIG. 5 depicts an image of the target of FIG. 4 obtained in the inspection apparatus of FIG. 3.
Figure 12A:
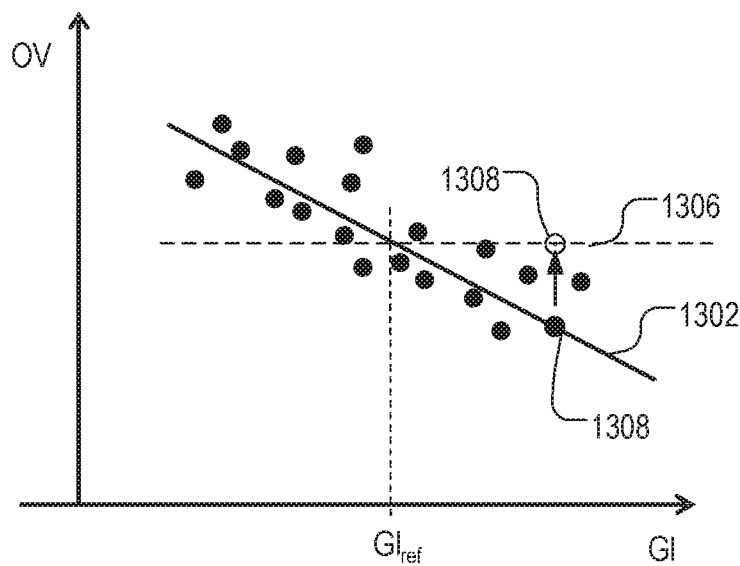
Figure 12B:
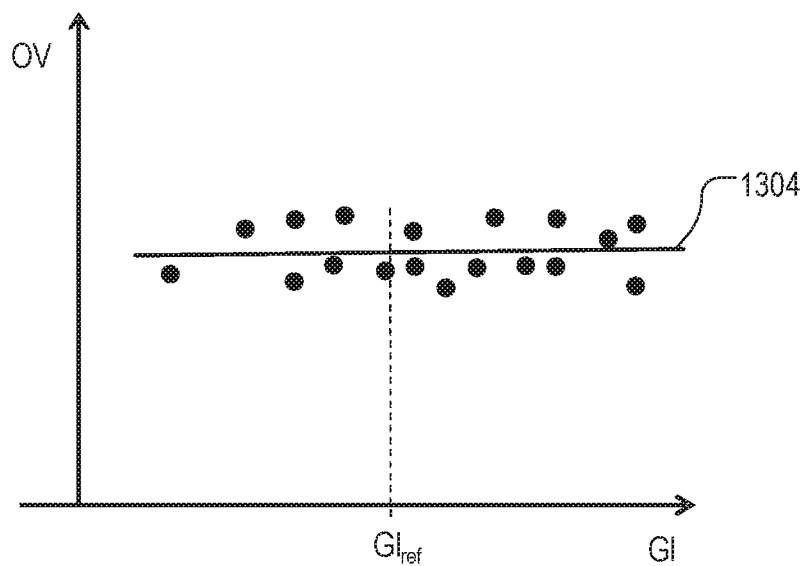
Figure 13:
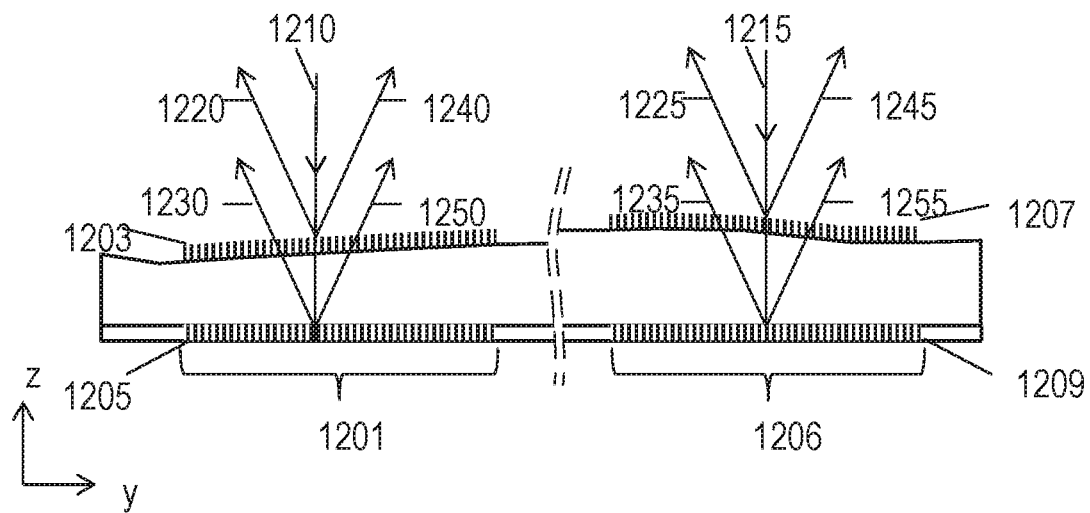
Figure 14:
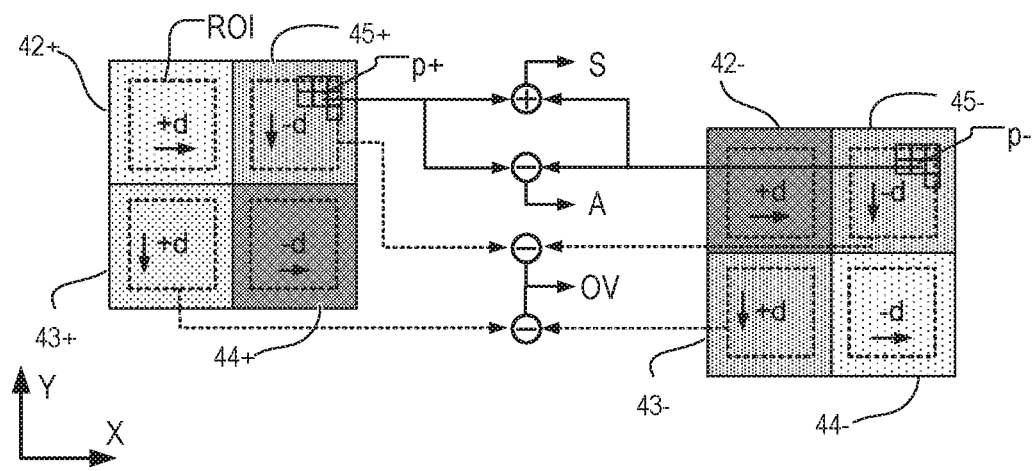
Figure 15A:
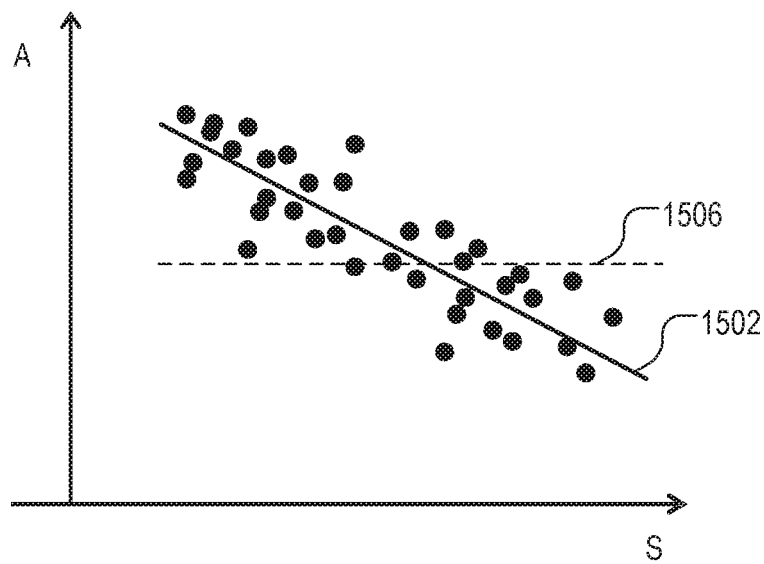
Figure 15B:
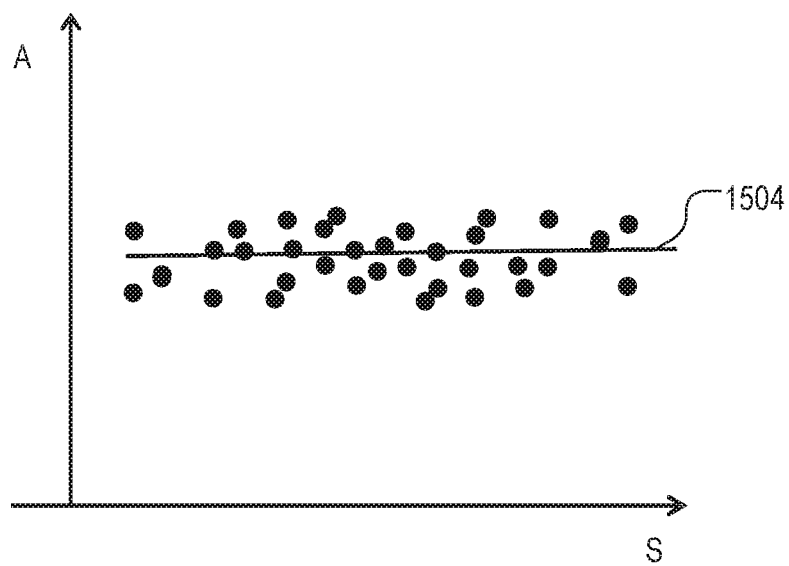
Figure 16:
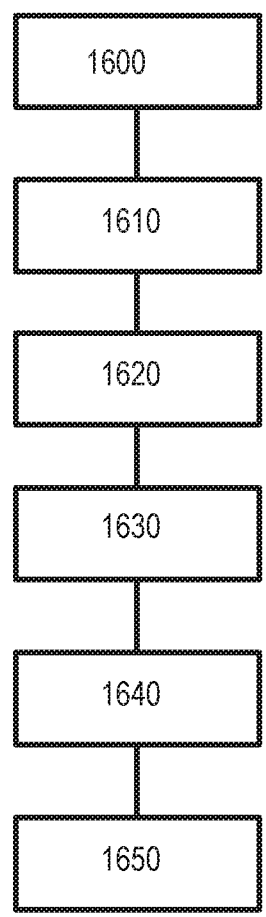

FIGS. 12A-12B illustrate the different performance of an overlay measurement method 12A using a recipe having a high sensitivity to stack difference (grating imbalance) and 12B using a recipe having low sensitivity to stack difference, and also illustrates a step of correcting an overlay measurement based on said sensitivity and a measured stack difference;

FIG. 13 schematically illustrates a situation where a stack difference exists between a first target periodic structure and a second target periodic structure and a stack difference exists also within each periodic structure;

FIG. 14 illustrates schematically the processing of signals for predicting sensitivity to stack difference in an overlay measurement based on images of a target similar to those of FIG. 5;

FIGS. 15A-15B depict examples of plots of asymmetry against symmetry resulting from the processing of FIG. 14, so as to distinguish using a recipe 15A having a high sensitivity to stack difference (grating imbalance) and a recipe 15B having low sensitivity to stack difference;

FIG. 16 is a flowchart of steps of a method according to an embodiment; and

Figure 17:
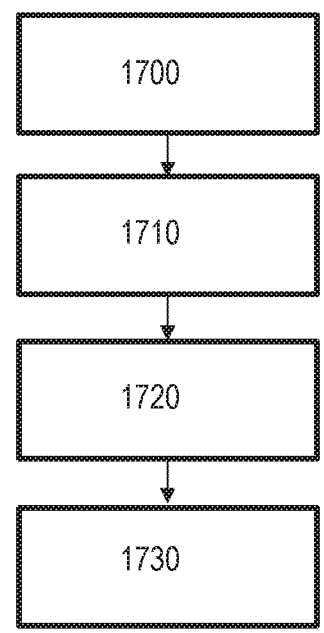

FIG. 17 is a flowchart illustrating a process in which a metrology target is used to monitor performance, and as a basis for controlling metrology, design and/or production processes.

DETAILED DESCRIPTION OF EXEMPLARY EMBODIMENTS

Before describing embodiments of the invention in detail, it is instructive to present an example environment in which embodiments of the present invention may be implemented.

Figure 1:
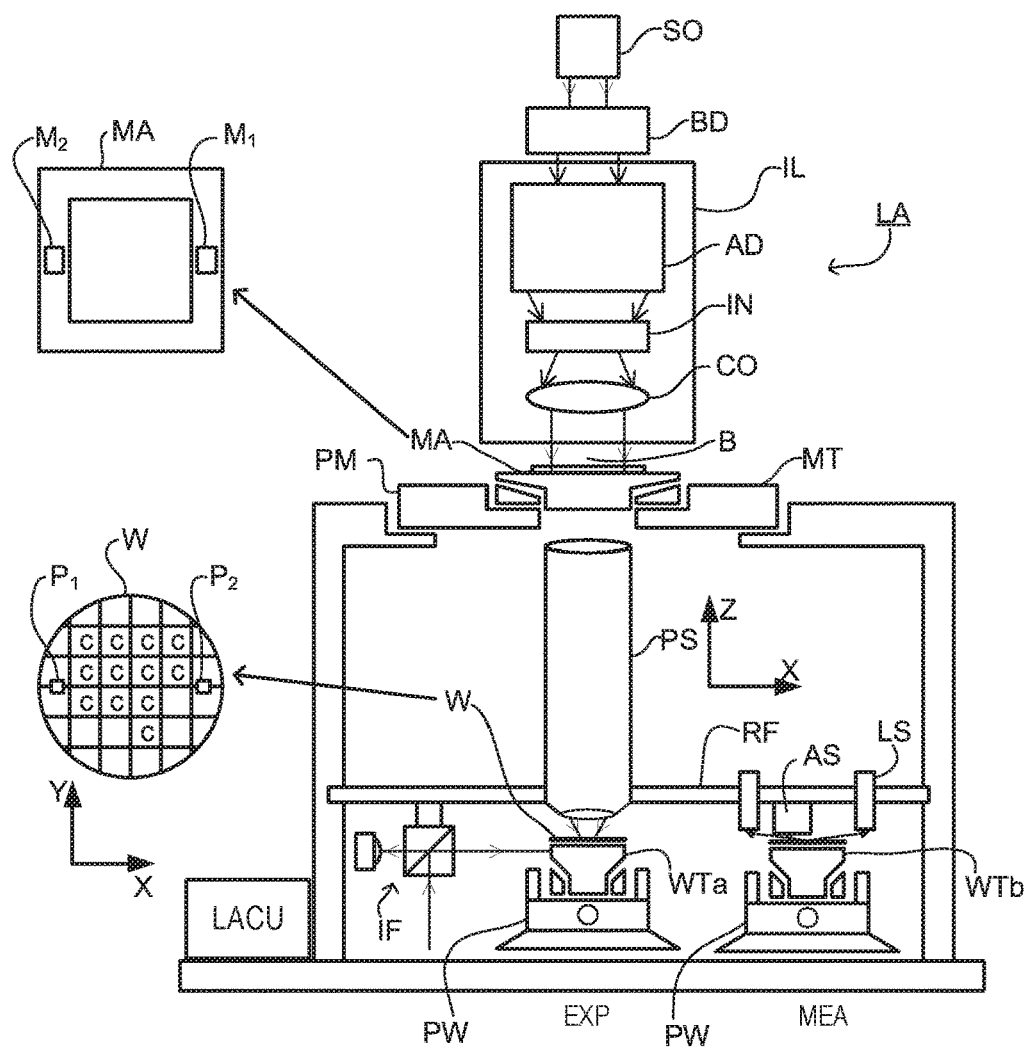
FIG. 1 depicts an embodiment of a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the marks be as small as possible and not require any different imaging or process conditions than adjacent features.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment marks on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

The apparatus further includes a lithographic apparatus control unit LACU which controls all the movements and measurements of the various actuators and sensors described. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these sub-systems.

Figure 2:
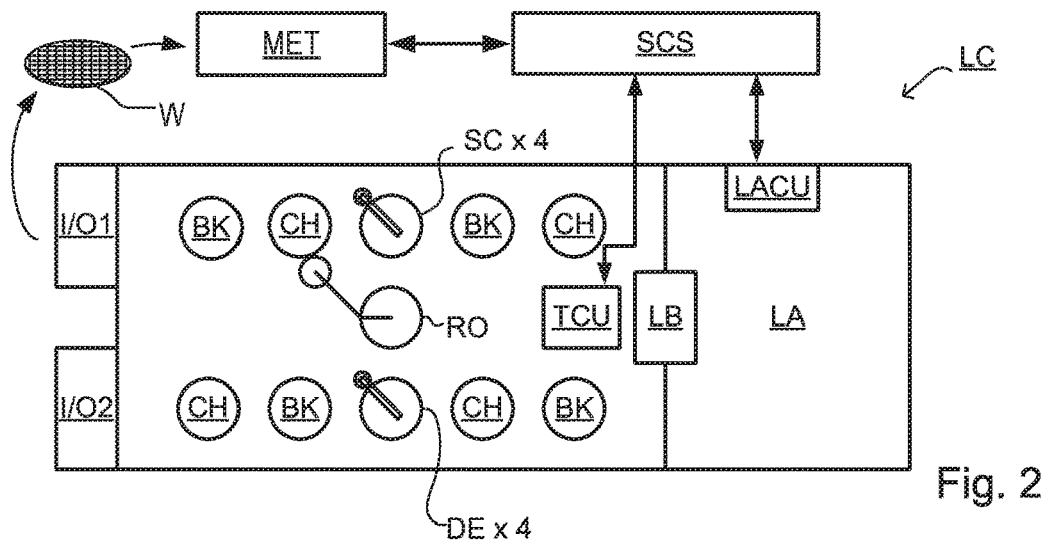
FIG. 2 depicts an embodiment of a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 3(b).

As described in the prior applications cited in the introduction, the dark-field -imaging apparatus of FIG. 3(a) may be part of a multi-purpose angle-resolved scatterometer that may be used instead of, or in addition to, a spectroscopic scatterometer. In this type of inspection apparatus, radiation emitted by a radiation source 11 is conditioned by an illumination system 12. For example, illumination system 12 may include a collimating lens system 12a, a color filter 12b, a polarizer 12c and an aperture device 13. The conditioned radiation follows an illumination path IP, in which it is reflected by partially reflecting surface 15 and focused into a spot S on substrate W via an objective lens 16. A metrology target T may be formed on substrate W. The objective lens 16 may be similar in form to a microscope objective lens, but has a high numerical aperture (NA), preferably at least 0.9 and more preferably at least 0.95. Immersion fluid can be used to obtain numerical apertures over 1 if desired.

The objective lens 16 in this example serves also to collect radiation that has been scattered by the target. Schematically, a collection path CP is shown for this returning radiation. The multi-purpose scatterometer may have two or more measurement branches in the collection path. The illustrated example has a pupil imaging branch comprising pupil imaging optical system 18 and pupil image sensor 19. An imaging branch is also shown, which will be described in more detail below. Additionally, further optical systems and branches will be included in a practical apparatus, for example to collect reference radiation for intensity normalization, for coarse imaging of capture targets, for focusing and so forth. Details of these can be found in the prior publications mentioned above.

Where a metrology target T is provided on substrate W, this may be a 1-D grating, which is printed such that, after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus. In the case of gratings, the structure is periodic. In the case of an overlay metrology target, the grating is printed on top of or interleaved with another grating that has been formed by a previous patterning step.

The various components of illumination system 12 can be adjustable to implement different metrology 'recipes' within the same apparatus. In addition to selecting wavelength (color) and polarization as characteristics of the illuminating radiation, illumination system 12 can be adjusted to implement different illumination profiles. The plane of aperture device 13 is conjugate with a pupil plane of objective lens 16 and with the plane of the pupil image detector 19. Therefore, an illumination profile defined by aperture device 13 defines the angular distribution of light incident on substrate W in spot S. To implement different illumination profiles, an aperture device 13can be provided in the illumination path. The aperture device may comprise different apertures 13a, 13b, 13c etc. mounted on a movable slide or wheel. It may alternatively comprise a fixed or programmable spatial light modulator (SLM). As a further alternative, optical fibers may be disposed at different locations in the illumination pupil plane and used selectively to deliver light or not deliver light at their respective locations. These variants are all discussed and exemplified in the documents cited above. The aperture device may be of a reflective form, rather than transmissive. For example, a reflective SLM might be used. Indeed, in an inspection apparatus working in the UV or EUV waveband most or all of the optical elements may be reflective.

Depending on the illumination mode, example rays 30a may be provided so that the angle of incidence is as shown at 'I' in FIG. 3(b). The path of the zero order ray reflected by target T is labeled '0' (not to be confused with optical axis 'O'). Similarly, in the same illumination mode or in a second illumination mode, rays 30b can be provided, in which case the angles of incidence and reflection will be swapped compared with the first mode. In FIG. 3(a), the zero order rays of the first and second example illumination modes are labeled 0a and 0b respectively.

As shown in more detail in FIG. 3(b), target grating T as an example of a target structure is placed with substrate W normal to the optical axis O of objective lens 16. In the case of an off-axis illumination profile, a ray 30a of illumination I impinging on grating T from an angle off the axis 0 gives rise to a zeroth order ray (solid line 0 ) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, the diffracted radiation of each order +1 and −1 will be further spread over a range of angles, not a single ideal ray as shown.

In the branch of the collection path for dark-field imaging, imaging optical system 20 forms an image T' of the target on the substrate W on sensor 23 (e.g. a CCD or CMOS sensor). An aperture stop 21 is provided in a plane in the imaging branch of the collection path CP which is conjugate to a pupil plane of objective lens 16. Aperture stop 21 may also be called a pupil stop. Aperture stop 21 can take different forms, just as the illumination aperture can take different forms. The aperture stop 21, in combination with the effective aperture of lens 16, determines what portion of the scattered radiation is used to produce the image on sensor 23. Typically, aperture stop 21 functions to block the zeroth order diffracted beam so that the image of the target formed on sensor 23 is formed only from the first order beam(s). In an example where both first order beams were combined to form an image, this would be the so-called dark field image, equivalent to dark-field microscopy.

The images captured by sensor 23 are output to image processor and controller PU, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose. Special designs of targets are provided to allow these measurements of different performance parameters to be made through the same basic asymmetry measurement method.

Processor and controller PU also generates control signals such as λ, p and AP, for controlling the illumination characteristics (polarization, wavelength) and for selecting the aperture using aperture device 13 or a programmable spatial light modulator. Aperture stop 21 may also be controlled in the same way. Each combination of these parameters of the illumination and the detection is considered a "recipe" for the measurements to be made.

Referring again to FIG. 3(b) and the illuminating rays 30a, +1 order diffracted rays from the target grating will enter the objective lens 16 and contribute to the image recorded at sensor 23. Rays 30b are incident at an angle opposite to rays 30a, and so the −1 order diffracted rays enter the objective and contribute to the image. Aperture stop 21 blocks the zeroth order radiation when using off-axis illumination. As described in the prior publications, illumination modes can be defined with off-axis illumination in X and Y directions. Apertures 13c, 13e and 13f in the aperture device 13 of FIG. 3(a) include off-axis illumination in both X and Y directions. With appropriate processing of radiation in the collection path, measurements of target properties can be made simultaneously in both directions. Aperture 13c is a particular form of segmented aperture, described in more detail in US2010201963 A1 and US2016091422 A1, mentioned above.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture stop 21 could be used to pass substantially only one first order of diffracted light to the sensor. In a further example, a set of off-axis prisms 22 are used in combination with an on-axis illumination mode. These prisms define a segmented aperture in which rays in each quadrant are deflected slightly through an angle. This deflection in the pupil plane in has the effect of spatially separating the +1 and −1 orders in each direction in the image plane. In other words, the radiation of each diffraction order and direction forms an image to different locations on sensor 23 so that they can be detected and compared without the need for two sequential image capture steps. Effectively, separate images are formed at separated locations on the image sensor 23. In FIG. 3(a) for example, an image T'(+1a), made using +1 order diffraction from illuminating ray 30a, is spatially separated from an image T'(−1b) made using −1 order diffraction from illuminating ray 30b. This technique is disclosed in the above-mentioned published patent application US2011102753 A1, the contents of which are hereby incorporated by reference. 2nd, 3rd and higher order beams (not shown in FIG. 3) can be used in measurements, instead of, or in addition to, the first order beams. As a further variation, the off-axis illumination mode can be kept constant, while the target itself is rotated 180 degrees beneath objective lens 16 to capture images using the opposite diffraction orders.

While a conventional lens-based imaging system is illustrated, the techniques disclosed herein can be applied equally with plenoptic cameras, and also with so-called "lensless" or "digital" imaging systems. There is therefore a large degree of design choice, which parts of the processing system for the diffracted radiation are implemented in the optical domain and which are implemented in the electronic and software domains.

Figure 4:
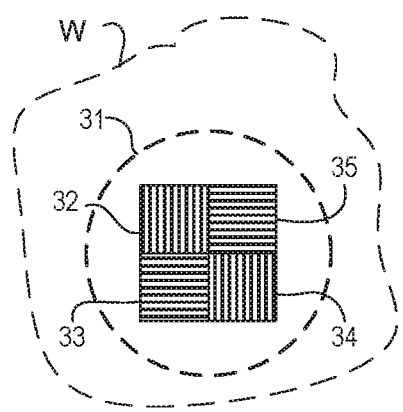
FIG. 4 depicts a form of multiple periodic structure target and an outline of a measurement spot on a substrate.

FIG. 4 depicts a composite target formed on a substrate W according to known practice. The composite target comprises four gratings 32 to 35 positioned closely together so that they will all be within the measurement spot S formed by the illumination beam of the metrology apparatus. A circle 31 indicates the extent of spot S on the substrate W. The four targets thus are all simultaneously illuminated and simultaneously imaged on sensor 23. In an example dedicated to overlay measurement, gratings 32 to 35 are themselves composite gratings formed by overlying gratings that are patterned in different layers of the semi-conductor device formed on substrate W. In this regard, the term "grating" should be understood as meaning any structure that is periodic in one or more direction. Gratings 32 to 35 may have differently biased overlay offsets in order to facilitate measurement of overlay between the layers in which the different parts of the composite gratings are formed. Gratings 32 to 35 may also differ in their orientation, as shown, so as to diffract incoming radiation in X and Y directions. In one example, gratings 32 and 34 are X-direction gratings with biases of the +d, −d, respectively. This means that grating 32 has its overlying components arranged so that if they were both printed exactly at their nominal locations one of the components would be offset relative to the other by a distance d. Grating 34 has its components arranged so that if perfectly printed there would be an offset of d but in the opposite direction to the first grating and so on. Gratings 33 and 35 are Y-direction gratings with offsets +d and −d respectively. Separate images of these gratings can be identified in the image captured by sensor 23. While four gratings are illustrated, another embodiment might require a larger matrix to obtain the desired accuracy.

FIG. 5 shows an example of an image that may be formed on and detected by the sensor 23, using the target of FIG. 4 in the apparatus of FIG. 3, and using an illumination profile providing off-axis illumination in both X and Y orientations simultaneously. The dark rectangle 40 represents the field of the image on the sensor, within which the illuminated spot 31 on the substrate is imaged into a corresponding circular area 41. Within this, rectangular areas 42 -45 represent the images of the small target gratings 32 to 35. If the gratings are located in product areas, product features may also be visible in the periphery of this image field. Image processor and controller PU processes these images using pattern recognition to identify the separate images 42 to 45 of gratings 32 to 35. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

In embodiments using the prism device 22, multiple grating images similar to that shown in FIG. 5 may be captured simultaneously within the field 40 of the sensor 23. As described above with reference to FIG. 3(a), images formed with opposite diffraction orders (for example +1 and −1 orders) can be found at different locations spatially separated within the same captured image.

Once the separate images of the gratings have been identified, the intensities of those individual images can be measured, e.g., by averaging or summing selected pixel intensity values within the identified areas. Intensities and/or other properties of the images can be compared with one another to obtain measurements of asymmetry for the four or more gratings simultaneously. These results can be combined with knowledge of the target structures and bias schemes, to measure different parameters of the lithographic process. Overlay performance is an important example of such a parameter, and is a measure of the lateral alignment of two lithographic layers. Overlay can be defined more specifically, for example, as the lateral position difference between the center of the top of a bottom grating and the center of the bottom of a corresponding top-grating. To obtain measurements of other parameters of the lithographic process, different target designs can be used. Again, knowledge of the target designs and bias schemes can be combined with asymmetry measurements to obtain measurements of the desired performance parameter. Target designs are known, for example, for obtaining measurements of dose or focus from asymmetry measurements obtained in this way.

In addition to asymmetry measurements by dark-field imaging of the type described above, measurements of overlay and other parameters can be made by direct imaging of targets.

The amount and accuracy of metrology required in an industry such as semiconductor manufacture is always increasing.

Figure 6:
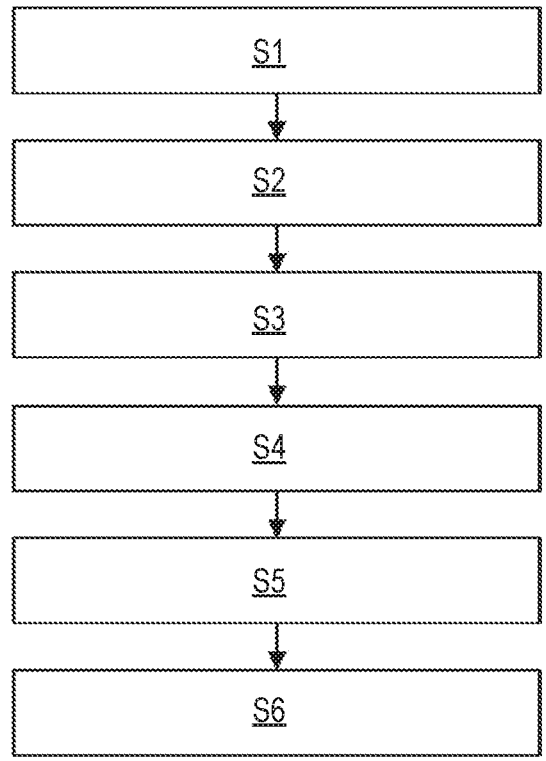
FIG. 6 is a flowchart showing steps of an overlay measurement method using the inspection apparatus of FIG. 3.

FIG. 6 illustrates how, using for example the method described in patent application publication US 2011027704 A1, overlay error (i.e., undesired and unintentional overlay misalignment) between the two layers containing the component periodic structures, i.e. gratings 32 to 35 is measured. This measurement is done through identifying target asymmetry, as revealed by comparing the intensities in the $+1^{st}$ order and $-1^{st}$ order dark field images of the target gratings (the intensities of other corresponding higher orders can be compared, e.g. $+2^{nd}$ and $-2^{nd}$ orders) to obtain a measure of the intensity asymmetry. At step S1, the substrate, for example a semiconductor wafer, is processed through a lithographic apparatus, such as the lithographic cell of FIG. 2, one or more times, to create a target including the gratings 32-35. At S2, using the inspection apparatus of FIG. 3, an image of the gratings 32 to 35 is obtained using only one of the first order diffracted beams (say −1 ). At step S3, whether by changing the illumination mode, or changing the imaging mode, or by rotating substrate W by 180° in the field of view of the inspection apparatus, a second image of the gratings using the other first order diffracted beam (+1 ) can be obtained. Consequently the +1 diffracted radiation is captured in the second image. Steps S2 and S3 can be performed simultaneously in an embodiment using suitable illumination with the prisms 21b. In that case, the first image and second image are obtained separated spatially in the field of image sensor 23.

Note that, by including only half of the first order diffracted radiation in each image, the 'images' referred to here are not conventional dark field microscopy images. The individual target features of the target gratings will not be resolved. Each target grating will be represented simply by an area of a certain intensity level. In step S4, a region of interest (ROI) is identified within the image of each component target grating, from which intensity levels will be measured.

Having identified the ROI for each individual target grating and measured its intensity, the asymmetry of the target, and hence overlay error, can then be determined. This is done (e.g., by the processor PU) in step 55 comparing the intensity values obtained for $+1^{st}$ and $-1^{st}$ orders for each target grating 32-35 to identify their intensity asymmetry, e.g., any difference in their intensity. The term "difference" is not intended to refer only to subtraction. Differences may be calculated in ratio form. In step S6 the measured intensity asymmetries for a number of target gratings are used, together with knowledge of any known imposed overlay biases of those target gratings, to calculate one or more performance parameters of the patterning process in the vicinity of the target T.

A performance parameter of great interest is overlay. As will be described later, other parameters of performance of the patterning process can be calculated. The performance parameter (e.g., overlay, CD, focus, dose, etc.) can be fed back (or fed forward) for improvement of the patterning process, improvement of the target, and/or used to improve the measurement and calculation process of FIG. 6 itself.

In the patent application publications mentioned above, various techniques are disclosed for improving the quality of overlay measurements using the basic method mentioned above. These techniques will not be explained here in further detail. They may be used in combination with the techniques newly disclosed in the present application.

Further, a metrology target measurement recipe can be used that specifies one or more parameters of the measurement using the measurement system. In an embodiment, the term "metrology target measurement recipe" includes one or more parameters of the measurement itself, one or more parameters of a pattern measured, or both.

In this context, a pattern measured (also referred to as a "target" or "target structure") may be a pattern that is optically measured, e.g., whose diffraction is measured. The pattern measured may be a pattern specially designed or selected for measurement purposes. Multiple copies of a target may be placed on many places on a substrate. For example, a metrology target measurement recipe may be used to measure overlay. In an embodiment, a metrology target measurement recipe may be used to measure another process parameter (e.g., dose, focus, CD, etc.) In an embodiment, a metrology target measurement recipe may be used for measuring alignment of a layer of a pattern being imaged against an existing pattern on a substrate; for example, a metrology target measurement recipe may be used to align the patterning device to the substrate, by measuring a relative position of the substrate.

In an embodiment, if the metrology target measurement recipe comprises one or more parameters of the measurement itself, the one or more parameters of the measurement itself can include one or more parameters relating to a measurement beam and/or measurement apparatus used to make the measurement. For example, if the measurement used in a metrology target measurement recipe is a diffraction-based optical measurement, one or more parameters of the measurement itself may include a wavelength of measurement radiation, and/or a polarization of measurement radiation, and/or measurement radiation intensity distribution, and/or an illumination angle (e.g., incident angle, azimuth angle, etc.) relative to the substrate of measurement radiation, and/or the relative orientation relative to a pattern on the substrate of diffracted measurement radiation, and/or number of measured points or instances of the target, and/or the locations of instances of the target measured on the substrate. The one or more parameters of the measurement itself may include one or more parameters of the metrology apparatus used in the measurement, which can include detector sensitivity, numerical aperture, etc.

In an embodiment, if the metrology target measurement recipe comprises one or more parameters of a pattern measured, the one or more parameters of the pattern measured may include one or more geometric characteristics (such as a shape of at least part of the pattern, and/or orientation of at least part of the pattern, and/or a pitch of at least part of the pattern (e.g., pitch of a grating including the pitch of an upper grating in a layer above that of a lower grating and/or the pitch of the lower grating), and/or a size (e.g., CD) of at least part of the pattern (e.g., the CD of a feature of a grating, including that of a feature of the upper grating and/or the lower grating), and/or a segmentation of a feature of the pattern (e.g., a division of a feature of a grating into sub-structures), and/or a length of a grating or of a feature of the grating), and/or a materials property (e.g., refractive index, extinction coefficient, material type, etc.) of at least part of the pattern, and/or an identification of the pattern (e.g., distinguishing a pattern being from another pattern), etc.

A metrology target measurement recipe may be expressed in a form like $(r_1, r_2, r_3, \ldots r_n; t_1, t_2, t_3, \ldots t_m)$, where $r_i$ are one or more parameters of the measurement and $t_j$ are one or more parameters of one or more patterns measured. As will be appreciated, n and m can be 1. Further, the metrology target measurement recipe does not need to have both one or more parameters of the measurement and one or more parameters of one or more patterns measured; it can have just one or more parameters of the measurement or have just one or more parameters of one or more patterns measured.

A target may be subjected to measurement using two metrology target measurement recipes A and B. The recipes may differ for example in the processing stage at which a target is measured (e.g., recipe A measures a target when it comprises a latent image structure and recipe B measures a target when it doesn't comprise a latent image structure) and/or differ on the parameters of their measurement. Metrology target measurement recipes A and B can at least differ on the target measured (e.g., recipe A measures a first target and recipe B measures a second different target). Metrology target measurement recipes A and B may differ on the parameters of their measurement of a target. Metrology target measurement recipes A and B may not even be based on the same measurement technique. For example recipe A may be based on diffraction-based measurement and recipe B may be based on scanning electron microscope (SEM) or atomic force microscopy (AFM) measurement.

Accordingly, in an embodiment, to determine one or more metrology target measurement recipes that would yield an accurate measurement of the desired process parameter (e.g., overlay) and/or that yields measurement values of the desired process parameter that is robust to process variability, a plurality of metrology target measurement recipes can be evaluated against one or more performance indicators to identify such one or more accurate and/or robust metrology target measurement recipes. Such a performance indicator is effectively a prediction of the performance of a measurement method. The measurement method in turn may be for measuring the performance of a process such as a lithographic process.

Now, FIG. 7 shows schematic cross sections of target gratings (overlay gratings), with different bias offsets. These can be used as the component gratings 32, 33 etc. in the composite target T on substrate W, as seen in FIGS. 3 and 4. Gratings with periodicity in the X direction are shown for the sake of example only. Different combinations of these gratings with different biases and with different orientations can be provided separately or as part of a composite target or a set of individual targets.

Starting with FIG. 7(a), a target 600 is formed in at least two layers, labeled L1 and L2. In the lower or bottom layer L1, a first periodic structure (the lower or bottom grating), for example a grating, is formed by features 602 and spaces 604 on a substrate 606. In layer L2, a second periodic structure, for example a grating, is formed by features 608 and spaces 610. (The cross-section is drawn such that the features 602, 608 (e.g., lines) extend into the page.) The grating pattern repeats with a pitch P in both layers. Features 602 and 608 may take the form of lines, dots, blocks and via holes. Together they may be referred to as an overlay grating. In the situation shown at FIG. 7(a), there is no overlay contribution due to misalignment, e.g., no overlay error and no imposed bias, so that each feature 608 of the second structure lies exactly over a feature 602 in the first structure.

At FIG. 7(b), the same type of target is shown, but with a first known bias +d such that the features 608 of the first structure are shifted by a distance d to the right, relative to the features of the second structure. The bias distance d might be a few nanometers in practice, for example 10 nm -20 nm, while the pitch P is for example in the range 300-1000 nm, for example 500 nm or 600 nm. At FIG. 7(c), another target with a second known imposed bias -d, such that the features of 608 are shifted to the left, is depicted. The value of d need not be the same for each structure. Biased overlay gratings of this type shown at FIGS. 7(a) to 7(c) are described in the prior patent application publications mentioned above.

FIG. 7(d) shows schematically a phenomenon of structural asymmetry, in this case structural asymmetry in the first periodic structure (bottom grating asymmetry). The features in the gratings at FIGS. 7(a) to 7(c), are shown as perfectly square-sided, when a real feature would have some slope on the side, and a certain roughness. Nevertheless they are intended to be at least symmetrical in profile. The features 602 and/or spaces 604 at FIG. 7(d) in the first periodic structure no longer have a symmetrical form at all, but rather have become distorted by one or more processing steps. Thus, for example, a bottom surface of each space has become tilted (bottom wall tilt). For example also, side wall angles of the features and spaces have become asymmetrical. As a result of this, the overall target asymmetry of a target will comprise an overlay contribution independent of structural asymmetry (i.e., an overlay contribution due to misalignment of the first structure and second structure; itself comprised of overlay error and any known bias) and a structural contribution due to this structural asymmetry in the target.

When overlay is measured by the method of FIG. 6 using only two biased gratings, the process-induced structural asymmetry cannot be distinguished from the overlay contribution due to misalignment, and overlay measurements (in particular to measure the undesired overlay error) become less reliable as a result. Structural asymmetry in the first periodic structure (bottom grating) of a target is a common form of structural asymmetry. It may originate, for example, in the substrate processing steps such as chemical-mechanical polishing (CMP), performed after the first structure was originally formed.

In patent application publication US 2013258310 A1, which is incorporated herein in its entirety by reference, three or more component gratings are used to measure overlay by a modified version of the method of FIG. 6. Three or more gratings of the type shown in FIGS. 7(a) to 7(c) are used to obtain overlay measurements that are to some extent corrected for structural asymmetry in the target gratings, such as is caused by bottom structure asymmetry in a practical patterning process. For simplicity in the present description, only the conventional structure with two biased gratings will be used to illustrate the principles of the present disclosure.

Figure 8:
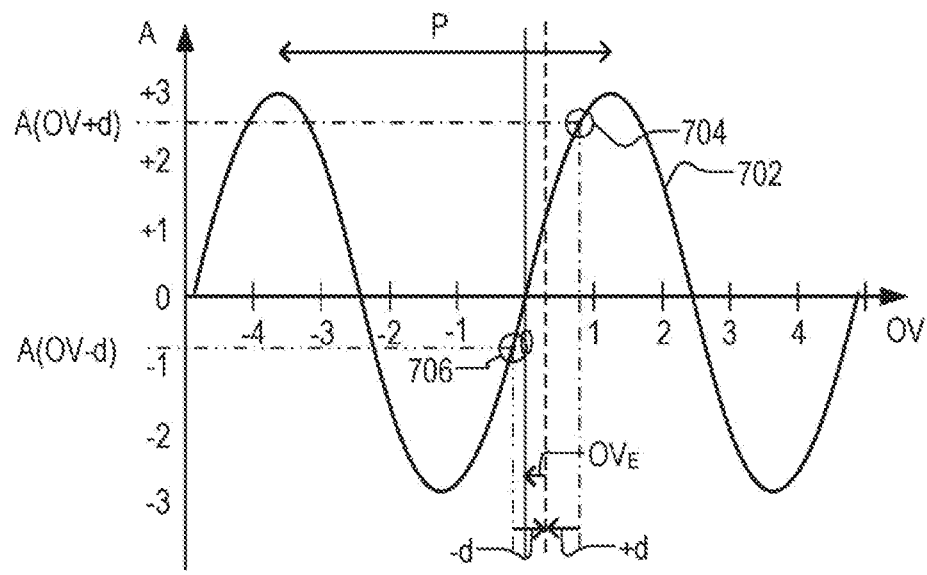
FIG. 8 illustrates principles of overlay measurement in an ideal target, not subject to structural asymmetry.
Figure 9:
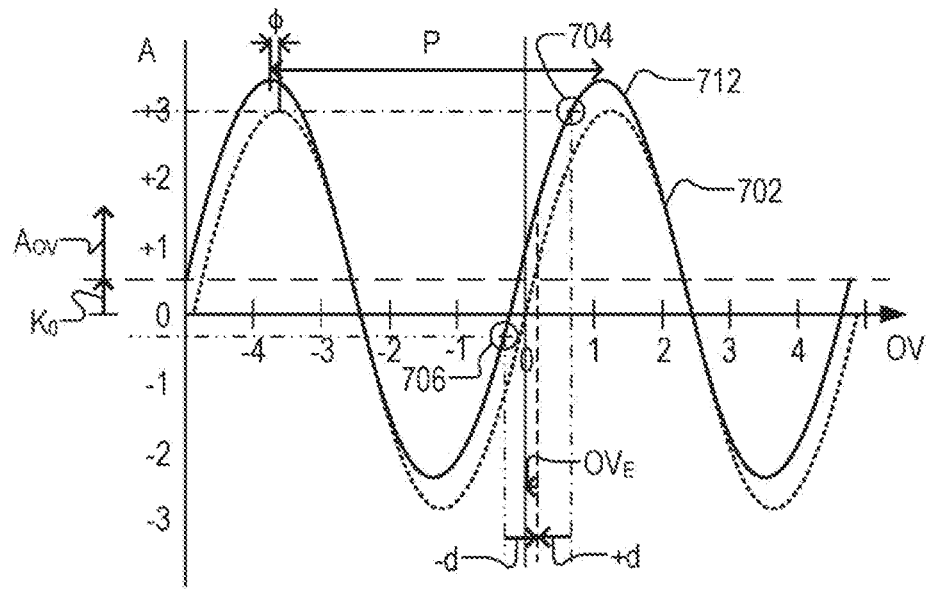
FIG. 9 illustrates principles of overlay measurement in a non-ideal target, with correction of structural asymmetry as disclosed in embodiments herein.

In FIG. 8 a curve 702 illustrates the relationship between overlay OV and intensity asymmetry A for an 'ideal' target having zero offset and no structural asymmetry within the individual gratings forming the target, and in particular within the bottom grating. Consequently, the target asymmetry of this ideal target comprises only an overlay contribution due to misalignment of the first structure and second structure resultant from a known imposed bias, and the unknown overlay error $OV_E$ which is in this example a performance parameter to be measured. This graph, and the graph of FIG. 9, illustrate the principles behind the measurement method only. In each graph, the units of intensity asymmetry A and overlay OV are arbitrary.

In the 'ideal' situation of FIG. 8, the curve 702 indicates that the intensity asymmetry A has a non-linear periodic relationship (e.g., sinusoidal relationship) with the overlay. The period P of the sinusoidal variation corresponds to the period or pitch P of the gratings, converted of course to an appropriate scale. The sinusoidal form is pure in this example, but can include harmonics in real circumstances.

As mentioned above, biased gratings (having a known imposed overlay bias) can be used to measure overlay, rather than relying on a single measurement. This bias has a known value defined in the patterning device (e.g. a reticle) from which it was made, that serves as an on-substrate calibration of the overlay corresponding to the measured intensity asymmetry. In the drawing, the calculation is illustrated graphically. In steps S1-S5, intensity asymmetry measurements $A_{+d}$ and $A_{-d}$ are obtained for gratings having imposed biases +d and −d respectively (as shown in FIG. 7(b) and FIG. 7(c), for example). Fitting these measurements to the sinusoidal curve gives points 704 and 706 as shown. Knowing the biases, the true overlay error $OV_E$ can be calculated. The pitch P of the sinusoidal curve is known from the design of the target. The vertical scale of the curve 702 is not known to start with, but is an unknown factor which can be referred to as a 1st harmonic proportionality constant, $K_1$. This constant $K_1$ is a measure of the sensitivity of the intensity asymmetry measurements to the target.

In equation terms, the relationship between overlay error $OV_E$ and intensity asymmetry A is assumed to be:

$$A_{\pm d}=K_1 \sin(OV_E \pm d) \quad (1)$$

where overlay error $OV_E$ is expressed on a scale such that the target pitch P corresponds to an angle $2\pi$ radians. Using two measurements of gratings with different, known biases (e.g. +d and −d), the overlay error $OV_E$ can be calculated using:

$$OV_E = \mathrm{atan}\left(\frac{A_{+d}+A_{-d}}{A_{+d}-A_{-d}} \cdot \tan(d)\right) \quad (2)$$

FIG. 9 shows a first effect of introducing structural asymmetry, for example the bottom grating asymmetry illustrated in FIG. 7D. The 'ideal' sinusoidal curve 702 no longer applies. However, at least approximately, bottom grating asymmetry or other structural asymmetry has the effect of adding an intensity shift term $K_0$ and a phase shift term $\phi$ to the intensity asymmetry $A_{\pm d}$. The resulting curve is shown as 712 in the diagram, with label $K_0$ indicating the intensity shift term, and label $\phi$ indicating the phase offset term. The intensity shift term $K_0$ and phase shift term $\phi$ are dependent upon a combination of the target and a selected characteristic of the measurement radiation, such as the wavelength and/or polarization of the measurement radiation, and is sensitive to process variations. In equation terms, the relationship used for calculation in step S6 becomes:

$$A_{\pm d}=K_0+K_1 \sin(OV_E \pm d+\phi) \quad (3)$$

Where there is structural asymmetry, the overlay model described by equation (2) will provide overlay error values which are impacted by the intensity shift term K0 and phase shift term $\phi$, and will be inaccurate as a consequence. The structural asymmetry will also result in differences in measurements of the same target using one or more different measurement parameters (e.g., measurement beam wavelength and/or polarization), when mapping the overlay error, because intensity and phase shift are wavelength and/or polarization dependent.

The overlay calculations of modified step S6 rely on certain assumptions. Firstly, it is assumed intensity asymmetry behaves as a sine function of the overlay, with the period P corresponding to the grating pitch. These assumptions are valid for present overlay ranges. The number of harmonics can be designed to be small, because the small pitch-wavelength ratio only allows for a small number of propagating diffraction orders from the grating. However, in practice the overlay contribution to the intensity asymmetry due to misalignment may not necessarily be truly sinusoidal, and may not necessarily be completely symmetrical about OV=0.

In an embodiment, the target asymmetry of a target is determined, and therefore overlay which does not neglect the effect of the structural asymmetry, while allowing the use of current target designs such as those illustrated in FIG. 4, can be determined. This may be performed as a modification to step S6 in the method illustrated in FIG. 6. In an embodiment, the method can calculate overlay errors accurately using real substrate measurement data, and which can determine an optimal or desired metrology target measurement recipe for measuring a target. No simulation or reconstruction may be needed.

In particular, it has been observed that, for the overlay range of interest, both the intensity term and phase term of the overlay contribution due to structural asymmetry is independent of the overlay contribution due to misalignment.

So, the total overlay OV (i.e., the measured overlay) can be represented in terms of the overlay contribution due to structural asymmetry $OV_{SA}$ and an overlay contribution independent of structural asymmetry $OV_{NSA}$:

$$OV = OV_{NSA} + OV_{SA} \quad (4)$$

The overlay contribution independent of structural asymmetry $OV_{NSA}$ may comprise the overlay error $OV_E$ (any unintentional misalignment of the layers) and/or any known imposed bias d. Separating the overlay contribution due to structural asymmetry $OV_{SA}$ into constituent intensity term $OV_{SAI}$ and phase term $OV_{SA\phi}$ yields:

$$OV = OV_{NSA} + (OV_{SAI} + OV_{SA\phi}) \quad (5)$$

Further, it has been determined that the constituent intensity term $OV_{SAI}$ of the overlay contribution due to structural asymmetry is proportional to the structural asymmetry in the lower grating BGA (where y is a proportionality constant):

$$OV_{SAI} = \gamma * BGA \quad (6)$$

Assuming that there is a relationship G (which can be referred to as the process robustness index) between intensity term $OV_{SAI}$ and phase term $OV_{SA\phi}$:

$$OV_{SA\phi} = G * OV_{SAI} \quad (7)$$

then equation (5) can be rewritten as:

$$OV = OV_{NSA} + \gamma * BGA + G * OV_{SAI} \quad (8)$$
$$= OV_{NSA} + \gamma * BGA + G * \gamma * BGA$$
$$= OV_{NSA} + \xi_{BGA} * BGA$$

where $\xi_{BGA} = \gamma + G*\gamma$. Provided that the relationship function $\xi_{BGA}$ is constant across the substrate then, by determining relationship function $\xi_{BGA}$, it is possible to determine the overlay which is independent of structural asymmetry $OV_{NSA}$. This overlay measurement therefore does not include the overlay contribution due to structural asymmetry $OV_{SA}$, which combines the intensity term and phase term. A constant relationship function $\xi$ also indicates that the process robustness index G is also constant across the substrate, even with stack variation. So a constant relationship function $\xi$ indicates that the metrology target measurement recipe is robust to process variation.

The relationship function $\xi_{BGA}$ can be found by measuring the targets on a substrate using two different sets of measurement parameters. In this case:

$$OV_A = OV_{NSAA} + \xi_{BGA,A} * BGA_A$$

$$OV_B = OV_{NSAB} + \xi_{BGA,B} * BGA_B$$

$$\Delta OV = \xi_{BGA,A} * BGA_A - \xi_{BGA,B} * BGA_B + C \quad (9)$$

where the subscripts A and B denote terms attributable to measurements made using a set A of measurement parameters (recipe A) and a set B of measurement parameters (recipe B) respectively; and where $OV_A$ and $OV_B$ being the measured overlay with measurement parameter set A and measurement parameter set B respectively. $\Delta OV$ is the difference between the measured overlay $OV_A$ using measurement parameter set A and the measured overlay $OV_B$ using measurement parameter set B. Equation (9) is further based upon the assumption that $OV_{NSAA} = OV_{NSAB} = OV_{NSA}$. In other words, the overlay which is independent of structural asymmetry is assumed to be independent of the measurement parameters. It is only the structural asymmetry signal BGA which is dependent on measurement parameters.

Measurement parameter sets A and B can differ in wavelength and/or polarization of the measurement radiation.

In one embodiment, the relationship function $\xi_{BGA}$ E can be found by determining the relationship between the measured structural asymmetry in lower grating $BGA_A$ using measurement parameter set A, the measured structural asymmetry in lower grating $BGA_B$ using measurement parameter set B and the difference in overlay measurements $\Delta OV$ between measurement parameter sets A and B. Using $\xi_{BGA}$ the overlay $OV_{NSAA} = OV_{NSAB} = OV_{NSA}$ can be determined from equation (9).

Stack Difference and Grating Imbalance

In addition to or alternatively to structural asymmetry in a target, a stack difference between adjacent gratings of a target or between adjacent targets may be a factor that adversely affects the accuracy of measurement, such as overlay measurement. Component gratings of a composite target, being formed adjacent to one another, are expected to experience the same processing conditions. In an embodiment, gratings or targets are adjacent if within 200 µm of each other, within 150 µm of each other, within 100 µm of each other, within 75 µm of each other, within 50 µm of each other, within 40 µm of each other, within 30 µm of each other, within 20 µm of each other, or within 10 µm of each other.

Stack difference may be understood as an unintentional difference in physical configurations between component gratings of targets used in a given measurement method. Stack difference causes a difference in an optical property (e.g., intensity, polarization, etc.) of measurement radiation between the component gratings or targets that is due to other than overlay error, other than intentional bias and other than structural asymmetry common to the adjacent gratings or targets. Stack difference includes, but is not limited to, a thickness difference between the adjacent gratings or targets (e.g., a difference in thickness of one or more layers such that one grating or target is higher or lower than another grating or target designed to be at a substantially equal level), a refractive index difference between the adjacent gratings or targets (e.g., a difference in refractive index of one or more layers such that the combined refractive index for the one or more layers for one grating or target is different than the combined refractive index for the one or more layers for of another grating or target even though designed to have a substantially equal combined refractive index), a difference in material between the adjacent gratings or targets (e.g., a difference in the material type, material uniformity, etc. of one or more layers such that there is a difference in material for one grating or target from another grating or target designed to have a substantially same material), a difference in the grating period of the structures of adjacent gratings or targets (e.g., a difference in the grating period for one grating or target from another grating or target designed to have a substantially same grating period), a difference in depth of the structures of adjacent gratings or targets (e.g., a difference due to etching in the depth of structures of one grating or target from another grating or target designed to have a substantially same depth), a difference in width (CD) of the features of adjacent gratings or targets (e.g., a difference in the width of features of one grating or target from another grating or target designed to have a substantially same width of features), etc. In some examples, the stack difference is introduced by processing steps, such as CMP, layer deposition, etching, etc. in the patterning process.

FIG. 10 schematically illustrates a situation where no stack difference exists between adjacent gratings (e.g., component gratings) of a composite target. For the sake of simplicity, the structure asymmetry is not considered in this example. Further, in the example of FIGS. 10 and 11, overlay is considered as the measurement parameter. Appropriate adjustments would be made for different parameter measurements using a special target, such as CD, focus, dose, etc. In all of these cases, it is assumed that asymmetry in the component gratings is key to the measurement method.

Figure 10A:
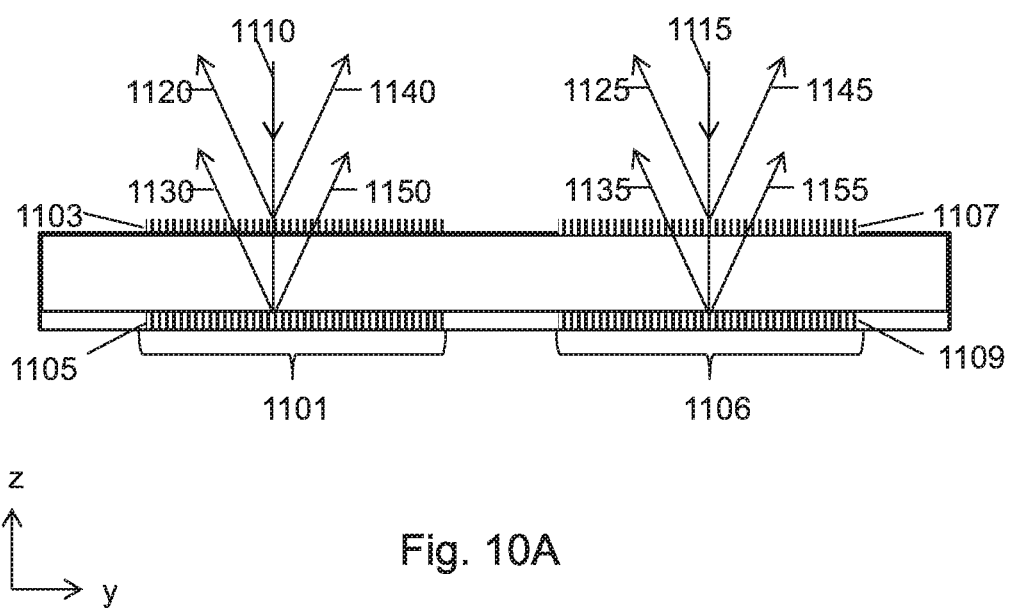
FIG. 10A schematically illustrates a situation where no stack difference exists between a first target periodic structure with a bias +d and a second target periodic structure with a bias −d, and illustrates diffraction signals following diffraction by the first and second target periodic structures.

FIG. 10A shows a first grating 1101 of a target has a bias +d and an adjacent second grating 1106 of the target has a bias −d. A first incident measurement radiation beam 1110 illuminates on the first structure 1105 and the second structure 1103 of the first grating 1101, where there is a bias +d between the first structure 1105 and the second structure 1103. As a result, −1$^{st}$ diffraction order signals 1130 and 1120 are diffracted by the first structure 1105 and the second structure 1103, respectively. The −1$^{st}$ diffraction order signal I'$_{-1}^{+d}$ by the first grating 1101 may be understood as the combination of the −1$^{st}$ diffraction order signals 1130 and 1120. Additionally, +1$^{st}$ diffraction order signals 1150 and 1140 are diffracted by the first structure 1105 and the second structure 1103, respectively. The +1$^{st}$ diffraction order signal I'$_{+1}^{+d}$ diffracted by the first grating 1101 may be understood as the combination of the +1$^{st}$ diffraction order signals 1150 and 1140. Accordingly, the −1$^{st}$ diffraction order signal I'$_{-1}^{+d}$ by the first grating 1101 and the +1$^{st}$ diffraction order signal I'$_{+1}^{+d}$ diffracted by the first grating 1101 may be collectively expressed by:

$$I'_{\pm 1}^{+d} = 1 + C^* \cos(\beta \pm \alpha_+) \quad (10)$$

where C indicates the contrast of the signal (which is a function of the grating design, measurement wavelength, etc.), $$\beta = 4\pi \frac{T}{\lambda},$$

T is me thickness of me first grating, λ is the measurement radiation wavelength, phase term $$\alpha_+ = 2\pi \frac{OV + d}{P},$$

OV is tne actual overlay error (OV$_E$ in the earlier description, due to any unintentional misalignment of the layers), and P is the pitch of the first structure 1105 and the second structure 1103 of the first grating 1101.

Figures 10B, 10C:
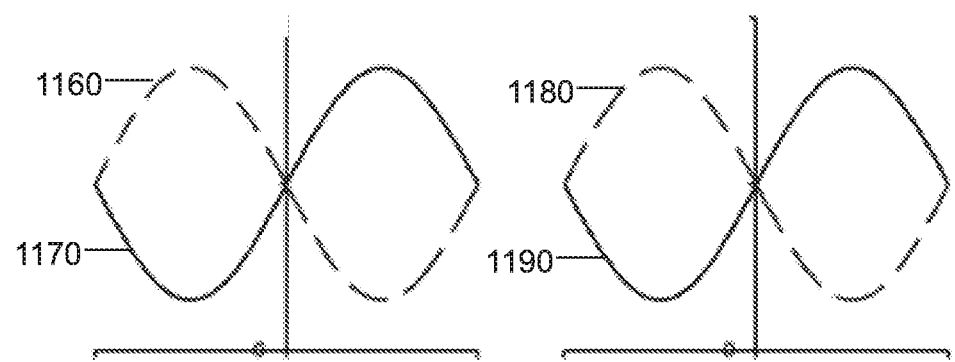
FIG. 10B schematically illustrates the intensity variations of the combined +1 st diffraction order signal and the combined −1 st diffraction order signal diffracted by the first target periodic structure.
FIG. 10C schematically illustrates the intensity variations of the combined +1 st diffraction order signal and the combined −1 st diffraction order signal diffracted by the second target periodic structure.

In FIG. 10B, the intensity profiles of the −1$^{st}$ diffraction order signal I'$_{-1}^{+d}$ by the first grating 1101, and the +1$^{st}$ diffraction order signal I'$_{+1}^{+d}$ diffracted by the first grating 1101, are depicted in traces 1160 and 1170, respectively according to equation (10).

Similarly, a second incident measurement radiation beam 1115 illuminates the first structure 1109 and the second structure 1107 of the second grating 1106, where there is a bias −d between the first structure 1109 and the second structure 1106. In the case of the dark-field imaging method illustrated in FIG. 3, the first and second incident measurement radiation beams 1110 and 1115 may be parts of the same illumination spot. As a result, −1$^{st}$ diffraction order signals 1135 and 1125 are diffracted by the first structure 1109 and the second structure 1107 of the second grating 1106, respectively. The −1$^{st}$ diffraction order signal I'$_{-1}^{-d}$ diffracted by the second grating 1106 may be understood as the combination of the −1$^{st}$ diffraction order signals 1135 and 1125. Additionally, +1$^{st}$ diffraction order signals 1155 and 1145 are diffracted by the first structure 1109 and the second structure 1107, respectively. The +1$^{st}$ diffraction order signal I'$_{+1}^{-d}$ diffracted by the second grating 1106 may be understood as the combination of the +1$^{st}$ diffraction order signals 1155 and 1145. Accordingly, the −1$^{st}$ diffraction order signal I'$_{-1}^{-d}$ diffracted by the second grating 1106 and the +1$^{st}$ diffraction order signal I'$_{+1}^{-d}$ diffracted by the second grating 1106 may be collectively expressed by:

$$I'_{\pm 1}^{-d} = 1 + C^* \cos(\beta \pm \alpha_-) \quad (11)$$

where C indicates the contrast of the respective signal, $$\beta = 4\pi \frac{T}{\lambda},$$

T is the thickness of the second grating, λ is the measurement radiation wavelength, phase term $$\alpha_- = 2\pi \frac{OV - d}{P},$$

OV is me actual overlay (due to any unintentional misalignment of the layers), and P is the pitch of the first structure 1109 and the second structure 1107 of the second grating 1106. In FIG. 10C, the intensity profiles of the −1$^{st}$ diffraction order signal diffracted by the second grating 1106 and the +1$^{st}$ diffraction order signal I'$_{+1}^{-d}$ diffracted by the second grating 1106 are depicted in traces 1180 and 1190, respectively according to equation (11).

Now, FIG. 11 illustrates a situation where a stack difference exists between a first grating 1201 with a bias +d and an adjacent second grating 1206 with a bias −d. In this case, purely by way of example, the stack difference is a difference in thickness between the layers, as shown in FIG. 11A and described hereafter. Similar to FIG. 10, a first incident measurement radiation beam 1210 illuminates the first structure 1205 of the first grating 1201 and the second structure 1203 of the first grating 1201, respectively. As a result, −1$^{st}$ diffraction order signals 1230 and 1220 are diffracted by the first structure 1205 and the second structure 1203, respectively. Accordingly, the −1$^{st}$ diffraction order signal I$_{-1}^{-d}$ diffracted by the first grating 1201 may be understood as the combination of the −1$^{st}$ diffraction order signals 1230 and 1220. Additionally, +1$^{st}$ diffraction order signals 1250 and 1240 are diffracted by the first structure 1205 and the second structure 1203, respectively. Accordingly, the +1$^{st}$ diffraction order signal I$_{+1}^{-d}$ diffracted by the first grating 1201 may be understood as the combination of the +1$^{st}$ diffraction order signals 1250 and 1240.

Similarly, a second incident measurement radiation beam 1215 illuminates the first structure 1209 and the second structure 1207 of the second grating 1206, respectively. As a result, −1$^{st}$ diffraction order signals 1235 and 1225 are diffracted by the first structure 1209 and the second structure 1207, respectively. Accordingly, the −1$^{st}$ diffraction order signal I$_{-1}^{+d}$ diffracted by the second grating 1206 may be understood as the combination of the −1$^{st}$ diffraction order signals 1225 and 1235. Additionally, +1$^{st}$ diffraction order signals 1255 and 1245 are diffracted by the first structure 1209 and the second structure 1207, respectively. Accordingly, the +1$^{st}$ diffraction order signal I$_{+1}^{+d}$ diffracted by the second grating 1206 may be understood as the combination of the +1$^{st}$ diffraction order signals 1255 and 1245.

Figure 11A:
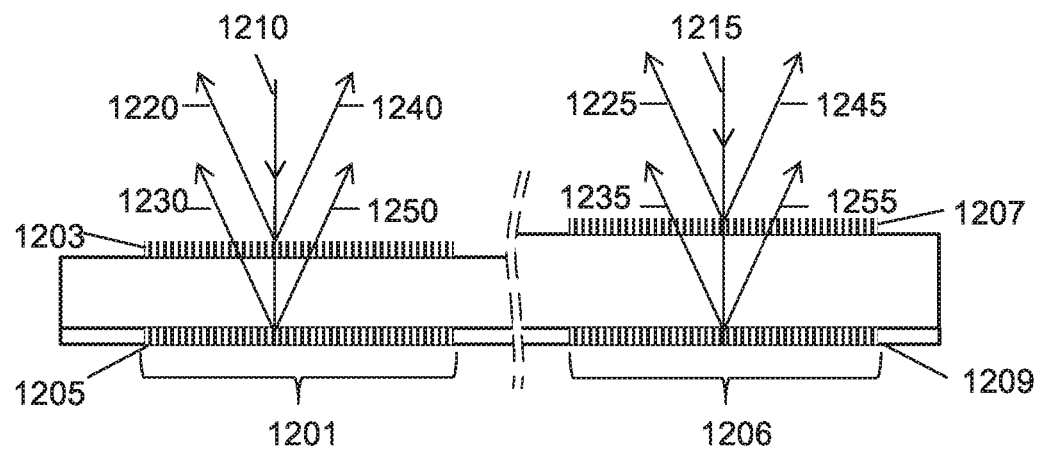
FIG. 11A schematically illustrates a situation where a stack difference exists between a first target periodic structure and a second target periodic structure, and illustrates diffraction signals following diffraction by the first and second target periodic structures.

As an example of stack difference, one or more layers between the first grating 1201 and the second grating 1206 may have a difference in thickness as shown in FIG. 11A. However, in another example, the stack difference may be created by one or more other factors that allow for an additional or alternative unintentional difference in physical configuration between the first grating 1201 and the second grating 1206. For example, a stack difference may be created when the first grating 1201 is more opaque to the first measurement radiation beam 1210 than the second grating 1206. For example, there may be a difference in material (e.g., a same type of material having a different refractive index, a different type of material, etc.) between the first grating 1201 and the second grating 1206. As another example, there may be a difference in pitch of the first grating 1201 relative to the second grating 1206 even though they are designed to have substantially the same pitch. These examples of stack difference are not the only ways there can be a stack difference and so should not be considered as limiting.

Referring back to equations (10) and (11), the stack difference may introduce three additional terms in each of equations (10) and (11). The first term, $\Delta I_N$, indicates an actual change to the intensity of the respective signal. The second term, $\Delta C_N$, indicates an actual change to the contrast of the respective signal. The third term, $\Delta \beta$, indicates an actual change to the phase of the respective signal. The three terms are dependent on the wavelength and/or the polarization of the measurement radiation beams 1210 and 1215. So, in the presence of a stack difference, the $-1^{st}$ diffraction order signal $I_{-1}^{+d}$ diffracted by the first grating 1201 and the $+1^{st}$ diffraction order signal $I_{+1}^{+d}$ diffracted by the first grating 1201 may be collectively expressed by:

$$I_{\pm1}^{+d} = (1+\Delta I_N)^* \{1 + C^*(1+\Delta C_N)^* \cos[(\beta+\Delta\beta)\pm\alpha_+]\} \quad (12)$$

Figures 11B, 11C:
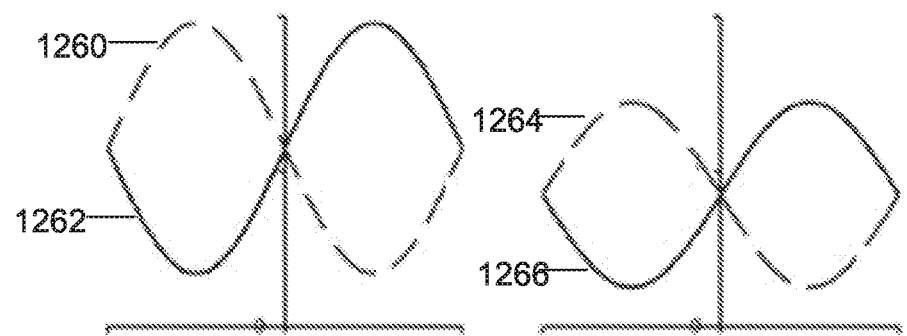
FIG. 11B and FIG. 11C schematically illustrates intensity variations of the combined +1 st diffraction order signal and the combined −1 st diffraction order signal diffracted by the first target periodic structure and the second target periodic structure, respectively.

In FIG. 11B, the intensity profiles of the $-1^{st}$ diffraction order signal $I_{-1}^{+d}$ diffracted by the first grating 1201 and the $+1^{st}$ diffraction order signal $I_{+1}^{+d}$ diffracted by the first grating 1201 are depicted in traces 1260 and 1262, respectively according to equation (12).

Figures 11D, 11E:
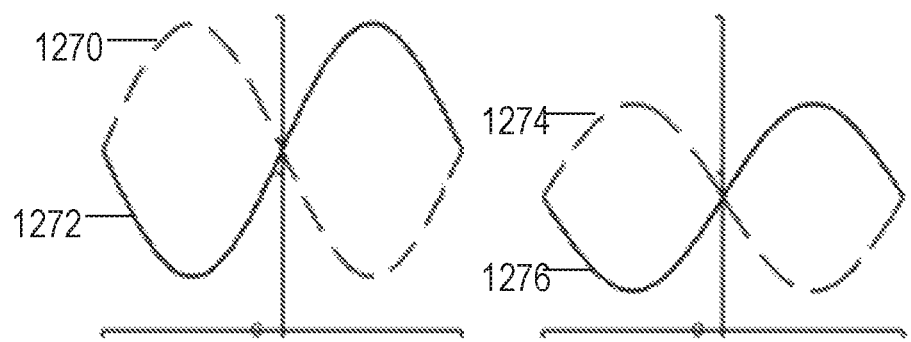
FIG. 11D and FIG. 11E illustrate contrast variations of the combined +1 st diffraction order signal and the combined −1 st diffraction order signal diffracted by the first target periodic structure and the second target periodic structure, respectively.

In FIG. 11D, the contrast profiles of the $-1^{st}$ diffraction order signal $I_{-1}^{+d}$ diffracted by the first grating 1201 and the $+1^{st}$ diffraction order signal $I_{+1}^{+d}$ diffracted by the first grating 1201 are depicted in traces 1270 and 1272, respectively according to equation (12).

Figures 11F, 11G:
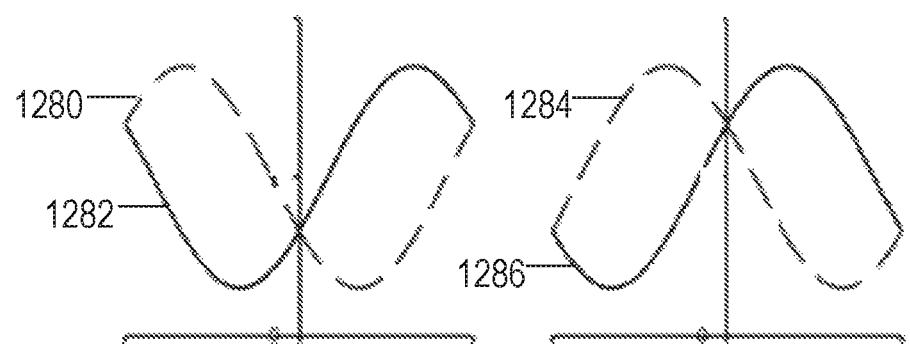
FIG. 11F and FIG. 11G illustrate phase variations of the combined +1 st diffraction order signal and the combined −1 st diffraction order signal diffracted by the first target periodic structure and the second target periodic structure, respectively.

In FIG. 11F, the phase profiles of the $-1^{st}$ diffraction order signal $I_{-1}^{-d}$ diffracted by the first grating 1201 and the $+1^{st}$ diffraction order signal $I_{+1}^{+d}$ diffracted by the first grating 1201, are depicted in traces 1280 and 1282, respectively according to equation (12).

Further, in the presence of the stack difference, the $-1^{st}$ diffraction order signal $I_{-1}^{-d}$ diffracted by the second grating 1206 and the $+1^{st}$ diffraction order signal $I_{+1}^{-d}$ diffracted by the second grating 1206 may be collectively expressed by:

$$I_{\pm1}^{-d} = (1+\Delta I_N)^* \{1 + C^*(1+\Delta C_N)^* \cos[(\beta+\Delta\beta)\pm\alpha_+]\} \quad (13)$$

In FIG. 11C, the intensity profiles of the $-1^{st}$ diffraction order signal $I_{-1}^{-d}$ diffracted by the second grating 1206, and the $+1^{st}$ diffraction order signal $I_{+1}^{-d}$ diffracted by the second grating 1206 are depicted in traces 1264 and 1266, respectively according to equation (13). Thus, compared to FIG. 11B, there is an intensity imbalance, which can lead to measurement error.

In FIG. 11E, the contrast profiles of the $-1^{st}$ diffraction order signal $I_{-1}^{-d}$ diffracted by the second grating 1206 and the $+1^{st}$ diffraction order signal $I_{+1}^{-d}$ diffracted by the second grating 1206 are depicted in traces 1274 and 1276, respectively according to equation (13). Thus, compared to FIG. 11D, there is a contrast imbalance, which can lead to measurement error.

In FIG. 11G, the phase profiles of the $-1^{st}$ diffraction order signal $I_{-1}^{-d}$ diffracted by the second grating 1206 and the $+1^{st}$ diffraction order signal $I_{+1}^{-d}$ diffracted by the second grating 1206 are depicted in traces 1284 and 1286, respectively according to equation (13). Thus, compared to FIG. 11F, there is a phase imbalance, which can lead to measurement error.

The measured intensity asymmetry of the first grating 1201, $\Delta I^{+d}$ is defined as:

$$\Delta I^{+d} = I_{+1}^{+d} - I_{-1}^{+d} \quad (14)$$

By incorporating equation (12) into equation (14) and assuming that $+\Delta I_N$ and $\Delta C_N$ are small, $\Delta I^{+d}$ can be expressed as:

$$\Delta I^{+d} \approx \frac{4\pi}{P} C(1 + \Delta I_N + \Delta C_N)\sin(\beta + \Delta\beta)(OV + d) \quad (15A)$$

And, the mean intensity $\hat{I}^{+d}$ can be expressed as:

$$\hat{I}^{+d} \approx 1 + \Delta I_N + C(1 + \Delta I_N + \Delta C_N)\cos(\beta + \Delta\beta)\left(q - 4\pi^2 \frac{dxOV}{P^2}\right) \quad (15B)$$

$$\text{where } q = 1 - \frac{2\pi^2}{P^2}(OV^2 + d^2)$$

Similarly, the measured intensity asymmetry of the second grating 1206, $\Delta I^{-d}$, is defined as:

$$\Delta I^{-d} = I_{+1}^{-d} - I_{-1}^{-d} \quad (16)$$

By incorporating equation (13) into equation (16) and assuming that $+\Delta I_N$ and $\Delta C_N$ are small, $\Delta I^{-d}$ can be expressed as:

$$\Delta I^{-d} \approx \frac{4\pi}{P} C(1 - \Delta I_N - \Delta C_N)\sin(\beta - \Delta\beta)(OV - d) \quad (17A)$$

And, the mean intensity $\hat{I}^{-d}$ can be expressed as:

$$\hat{I}^{-d} \approx 1 - \Delta I_N + C(1 - \Delta I_N - \Delta C_N)\cos(\beta - \Delta\beta)\left(q + 4\pi^2 \frac{dxOV}{P^2}\right) \quad (17B)$$

The measured overlay $OV_m$ can be calculated by:

$$OV_m = d * \frac{\Delta I^{+d} + \Delta I^{-d}}{\Delta I^{+d} - \Delta I^{-d}} \quad (18)$$

By incorporating equations (14)-(17) into equation (18), an error in overlay measurement $\Delta\varepsilon_{OV}$ can be obtained as:

$$\Delta\varepsilon_{OV} = OV_m - OV \approx d * \left[1 - \left(\frac{OV}{d}\right)^2\right] * [\cot(\beta) * \Delta\beta + \Delta I_N + \Delta C_N] \quad (19)$$

When $\beta \approx 90°$ (for a well-designed target) and the overlay (OV) is small (relative to the bias d), equation (19) may be further simplified as:

$$\Delta \varepsilon_{OV} = OV_m - OV \approx d*(\Delta I_N + \Delta C_N) \quad (20)$$

Further, when the first grating 1201 and the second grating 1206 are well designed with a contrast C equal to or approximately equal to 1, $\Delta C_N$ is approximately equal to zero. Therefore, the measurement error $\Delta \varepsilon_{OV}$ can be further simplified as:

$$\Delta \varepsilon_{OV} = OV_m - OV \approx d*\Delta I_N \quad (21)$$

As can be seen from equations (19)-(21), the measured overlay $OV_m$ differs from the actual overlay OV by a measurement error $\Delta \varepsilon_{OV}$ produced by the stack difference. Thus, accuracy in measurement can be improved by correcting for stack difference between the adjacent gratings or targets. The measurement error that arises from the stack difference may be corrected with changes to the process of creating or measuring the gratings or targets (e.g., process offsets) which are, for example, based on yield (i.e., evaluation of processed devices to determine whether the gratings or targets were accurate), evaluation of cross-sections of adjacent gratings or targets, or complex measurement and analytical reconstructions. These methods can be slow and/or destructive. They may only be effective to correct a constant process error. Further, variation in stack difference of the adjacent gratings or targets may not be effectively solved by cross-sections or yield measurements. Accordingly, there is a desire for, for example, a robust solution of evaluating and correcting for stack difference.

In order to characterize the stack difference, and the influence it has on the reported measurement, one or more stack difference parameters can be defined. A stack difference parameter may be a measure of the unintentional difference in physical configuration of the adjacent gratings or targets. Another stack difference parameter may be a measure of the sensitivity of the reported measurement to stack difference. The stack difference parameters can be used to predict the performance of the measurement method. Furthermore, if sufficient information is available per measurement, to correct measurements made using the gratings or targets. The corrected measurements naturally may be used in creating, qualifying, verifying, etc., for example, devices by a patterning process. Even if the measurements are uncorrected, information about the performance of the measurement method, either generally or for each particular target, can be used to adjust the influence which is given to the measurements in the control of the patterning process. Additionally or alternatively, the stack difference parameter can be used in the (re-)design of one or more of the targets (e.g., making a change to a layout of the design), may be used in the process of forming one or more of the adjacent gratings or targets (e.g., making a change in material, a change in a printing step or condition, etc.), may be used in formulation of the measurement conditions (e.g., make a change in the optical measurement formulation in terms of wavelength, polarization, illumination mode, etc. of the measurement beam), etc.

As an example of a stack difference parameter, an indication of 'imbalance' between the gratings can be obtained by comparing the average intensity of two grating images, formed using the $+1^{st}$ diffraction order and the $-1^{st}$ diffraction order, over the regions of interest (ROI) in images of the type shown in FIG. 5. This average intensity can be calculated in the same way as the asymmetry A, but is based on a sum, rather than a difference of the intensities recorded in the ROIs of the images of a grating. The average intensity may therefore be referred to as a "symmetry" property S of a grating, with the formulae for asymmetry and symmetry being:

$$A = I^+ - I^-$$

$$S = I^+ + I^- \quad (22)$$

where $I^+$ represents intensity of $+1^{st}$ diffraction order radiation and $I^-$ represents intensity of $-1^{st}$ order diffracted radiation.

Recall that the parameter overlay can be calculated from the same intensity values by the formula of Equation (23):

$$OV \approx d \frac{A_{+d} + A_{-d}}{A_{+d} - A_{-d}} \quad (23)$$

where suffixes +d and -d indicate differently biased gratings. From the difference in average intensity (symmetry) between two gratings in a composite target, a parameter "grating imbalance" can be obtained, for example by the formula:

$$GI = 2 \frac{S_{+d} - S_{-d}}{S_{+d} + S_{-d}} \quad (24)$$

This number GI will vary between target designs and processes, and between targets on the same substratum for reasons explained above. The reported grating imbalance will also vary between different measurement recipes, even for the same stack difference, and can be used to avoid selecting recipes that are particularly sensitive. That is to say, for a given target, one recipe may report a significant grating imbalance, while the other does not. Furthermore, however, it has been found that for two recipes that report more or less equal "grating imbalance", the impact on the overlay measurement (or other parameter of interest) can be vastly different. In other words the sensitivity of the measurement method to grating imbalance can vary significantly from setting to setting. This sensitivity of the measurement method to grating imbalance ("GI sensitivity") is an example of a performance parameter of the method that can be predicted by the method to be described below.

FIG. 12 illustrates schematically the reported overlay OV and grating imbalance GI when using two different measurement recipes (a) and (b) on the same target. To obtain each sample point, overlay and grating imbalance are calculated from images using the formulae above. To obtain a wide distribution of points, these samples are local overlay and GI values, obtained by processing small regions of the images within the ROIs, rather than the ROIs as a whole. The small regions in practice may be as small as individual pixels, but regions of a few of pixels could be chosen, if desired. In each plot, the samples are plotted against OV and GI. In plot (a) it is seen that the reported GI value varies widely about a mean value $GI_{ref}$, and there is a correlated variation in reported overlay. In plot (b), for the same target, there is a similar variation in grating imbalance, but the overlay value is not systematically affected by this.

By statistical analysis such as linear regression, a line is fitted to the plotted data in each plot. The line 1302 in plot (a) has a significant slope while the line 1304 in (b) is substantially horizontal. The slope of the line represents the sensitivity of the measurement method when recipe (a) or (b) is used, and can be used as a prediction of performance of the measurement method, with the benefits mentioned above. The recipe (b) could be chosen for measuring this type of target in future, for example, based on the lower slope of line 1304. Alternatively, where recipe (a) is used, the slope of line 1302 could be used to report an uncertainty value (error bars).

The slope and height of the line 1302 can also be used to calculate a correction based on the reported GI value and the reported overlay value, to adjust the reported overlay to a nominal line 1306. Thus, for example, the measurement method may include a correcting step in which a target having measured values of overlay and grating imbalance as plotted at 1308 is subject to a correction and reported with values corresponding to point 1310.

While being extremely valuable in principle, those benefits are only realized if the statistical analysis is available for every measurement. In order to calculate a 'pixel based' 'overlay' and 'grating imbalance', actually two pixels are needed: one in the positive biased grating and one in the negative bias grating. This combination can be made in many different ways from the intensity values in the ROI: one can combine them in their original orientation (e.g. combine the top-left pixel of the positive bias grating with the top-left pixel of the negative bias grating), or one can rotate the images with respect to each other (e.g. combining top-left of the PB grating with bottom right of the NB grating), or one can flip the image. Which of these many possibilities is the 'right' combination depends on the exact target layout and the type of processing effect present, and this is not a priori known.

To address that issue one could simply calculate the effect for all possible combinations of pixels. However, this can easily lead to a large computational effort, beyond what is available in real time, for high-volume manufacturing situations. Considering, for example, a case where each ROI consists of and area 50×50 pixels, such a calculation would require (50×50)×(50×50)=6250000 different pixel combinations. Consequently, to produce plots such as those in FIG. 12 for every measurement would be impractical.

The present inventor has recognized that equivalent predictions of performance of the measurement method can be obtained with only a single grating. Even if the prediction of performance would be calculated for different gratings to increase statistical relevance, the computational burden would still be limited, and readily achieved in real time. This insight can be explained as follows. Since Grating Imbalance as defined above is basically a difference in average intensity S of the two gratings, it can only change if the symmetry S (average intensity) of at least one of the gratings changes. At the same time, since overlay is calculated from the asymmetries A of the two gratings, and hence it can only change if the asymmetry of at least one of the two gratings changes. Therefore the information shown in the plots of FIG. 12 can also be found in the asymmetry vs intensity (or 'symmetry') plots of the individual gratings.

FIG. 13 illustrates how the stack and other properties of the gratings will in practice vary to some extent within each individual grating, and not only between different gratings. This variation is exploited in the disclosed method, in order to probe the response of the measurement method to a range of symmetry and asymmetry conditions.

FIG. 14 illustrates schematically the implementation of the method in one embodiment of the present disclosure. The grating images for a composite target are shown, in the same form as described above with reference to FIG. 4. At the left there are four grating images 42+to 45 +which are formed using (say) +1$^{st}$ order diffracted radiation, while on the right there are four grating images 42− to 45− of the same composite target are formed, but using −1$^{st}$ order diffracted radiation. (It is a matter of choice how to label the orders, and the +1$^{st}$ order and −1$^{st}$ order diffracted radiation of different component gratings could appear in the same image.)

As in the known measurement methods, average intensities from the whole ROIs are used to calculate overlay, or other asymmetry-related parameter of interest. This is illustrated in dotted lines for the Y-oriented gratings. The asymmetries are calculated for each grating, and then the asymmetries for the different biased gratings are combined to obtain an overlay value OV, based on Equation (23) above.

To obtain a prediction of performance of the overlay measurement method, additional, pixel level processing is represented by the solid lines. For each pixel p within the ROI of one pair of images, for example the images 45+ and 45−, a pixel-by pixel difference is made to calculate an asymmetry value A and a pixel-by-pixel average is made to calculate the symmetry value S. Given an ROI of, for example, 50×50 pixels, therefore 2500 individual sample points will be obtained. It is not absolutely necessary to use the pixels of the same ROI as the OV calculation. However by keeping them the same or similar, one may expect that the GI sensitivity is the most accurate for the particular OV measurement.

FIG. 15 shows plots (a) and (b) which look very similar to the plots in FIG. 12, but which are simply plots of the per-pixel asymmetry value A and symmetry value S. (For simplicity, fewer than 2500 points are shown.) Confirming that the assumptions behind this method are correct, the distributions of these sample points are found in real measurements to be very similar for the recipes (a) and (b) to the distributions of the overlay and grating imbalance values plotted in FIG. 12. However, because these values are derived only from the images of one grating, the complication and computational burden associated with the calculations of per-pixel overlay and grating imbalance is avoided. Statistical analysis such as linear regression is used to fit a line 1502 to the data distribution obtained by recipe (a) and to fit a line 1504 to the data obtained by recipe (b). As before, the slope of each line provides a prediction of performance of the measurement method according to the corresponding recipe. It can be seen that recipe (a) is a "bad" recipe and recipe (b) is a "good" recipe, at least from this performance parameter. As already discussed above, being able to predict performance of the measurement method in a parameter such as sensitivity to grating imbalance allows selection of recipes can be improved. Alternatively or in addition, reliability values (for example "error bars") can be reported along with the overlay values reported for the target as a whole. Knowing the overlay and grating imbalance reported for the whole ROI, the slope and height of the fitted line 1502 obtained from a single ROI can be used to apply a correction to the reported overlay measurement, normalizing the results from point 1308 to point 1310 as shown in FIG. 12 (a). The calculations illustrated in FIG. 14 and the data illustrated in FIG. 15 are easily accomplished in real time, alongside the measurement method itself.

In mathematical terms, the derivation of the calculation of GI sensitivity is as follows. Recalling the equations above for overlay and GI, derivatives of GI and OV can be calculated for the positively biased grating as:

$$\frac{dGI}{dS_{+d}} = 2\frac{1}{S_{+d} + S_{-d}}\left(1 - \frac{1}{2}GI\right) \text{ and} \quad (25)$$

$$\frac{dOV}{dA_{+d}} = \frac{d}{A_{+d} - A_{-d}}\left(1 - \frac{OV}{d}\right) \quad (26)$$

This yields an expression for GI sensitivity which is:

$$\frac{dOV}{dGI} = \frac{\frac{d}{A_{+d} - A_{-d}}\left(1 - \frac{OV}{d}\right)dA_{+d}}{2\frac{1}{S_{+d} + S_{-d}}\left(1 - \frac{1}{2}GI\right)dS_{+d}} = \frac{d}{SS} \cdot \left(\frac{1 - OV/d}{1 - \frac{1}{2}GI}\right) \cdot \frac{dA_{+d}}{dS_{+d}} \quad (27)$$

where SS is a "stack sensitivity" parameter calculated as:

$$SS = 2\frac{A_{+d} - A_{-d}}{S_{+d} + S_{-d}} \quad (28)$$

and where the term of the form $dA_{+d}/dS_{+d}$ is the slope of the relationship between asymmetry and symmetry, obtained by statistical analysis of the per-pixel asymmetry and symmetry values obtained by the method of FIGS. 14 and 15.

Generalizing the above expression for GI sensitivity we can write for the positively biased grating:

$$\frac{dOV}{dGI} \approx \frac{d}{SS} \cdot \left(\frac{1 - OV/d}{1 - GI/2}\right) \cdot \frac{dA}{dS}\bigg|_{+d} \quad (29)$$

and for the negatively biased grating:

$$\frac{dOV}{dGI} \approx \frac{d}{SS} \cdot \left(\frac{1 + OV/d}{1 + GI/2}\right) \cdot \frac{dA}{dS}\bigg|_{-d} \quad (30)$$

An approximation of the above equations can be written, assuming small values for OV relative to the bias values and assuming small GI also:

$$\frac{dOV}{dGI} \approx \frac{d}{SS} \cdot \frac{dA}{dS}\bigg|_{+d} \quad (31)$$

$$\frac{dOV}{dGI} \approx -\frac{d}{SS} \cdot \frac{dA}{dS}\bigg|_{-d}$$

Rewriting these equations for small OV and small GI the following relations apply:

$$\overline{A}_{-d} \approx -\overline{A}_{+d}$$

$$\overline{S}_{-d} \approx \overline{S}_{+d} \quad (32)$$

where the bars indicate the average of A and S values over all the individual pixels.

Substituting these into the equation for GI sensitivity, we find that the equations for both gratings become the same:

$$\frac{dOV}{dGI} \approx \frac{d}{2} \cdot \frac{d(A/\overline{A})}{d(S/\overline{S})} \quad (33)$$

and this equation (33) provides the formula for calculating GI sensitivity as a prediction of performance of the method of measuring overlay, according to the recipe used to obtain the grating images. Therefore it is proposed to determine the sensitivity to grating imbalance in this way, by determining the relation between asymmetry (the difference between $+1^{st}$ and $-1^{st}$ orders) and 'symmetry' (the sum or average of the $+1^{st}$ and $-1^{st}$ orders).

This GI sensitivity value can be determined for every captured ROI, and therefore there is no need to worry about the correct orientation of the ROIs, and the computational effort is much reduced compared to the permutations required to calculate per-pixel overlay and per-pixel GI. In principle a single ROI is sufficient, but in general there will be at least two. The two slopes are typically similar, since the characteristics of the two gratings cannot be very different. To summarize the two slopes into a single number they can for example be averaged. This can easily be extended to multi-bias scenarios where there are more than two grating pads per direction. It is assumed that GI sensitivity and GI may be quite different between the X and Y directions, and therefore one would measure and calculate all parameters separately for X and Y.

Since this computation is simple and can be done quickly, the sensitivity can be calculated and reported at every single point. It may be combined with the normal Grating Imbalance to create an "overlay impact number", expressed for example in nanometers, that can also be reported per point. The overlay impact number, specific to a particular measurement, can further be used to correct the overlay value. These values can be used during recipe selection, to avoid bad settings, or they can be used during run-time to check the reliability of the measurement and to check whether the chosen recipe is still a good choice (this may have changed for example due to drifts in the process). These values can equally be used in the design of new metrology targets, to reduce GI sensitivity under a given measurement recipe.

Not only the measurement recipe, but also metrology target designs may be varied in a number of ways. There may be variation in one or more parameters such as critical dimension, sidewall angle, pitch, etc. A number of candidate metrology target designs may be evaluated, each showing variation in one or more of these parameters. Similarly, measurement characteristics may be varied in terms of parameters such as wavelength and/or polarization. So, a plurality of metrology target measurement recipes may be evaluated, each recipe showing variation in one or more of these parameters.

FIG. 16 is a flowchart of a method of metrology target measurement recipes selection according to an exemplary embodiment. At 1600, measurement radiation intensity values for a first metrology target measurement recipe are captured and local asymmetry and symmetry values are obtained (for example per-pixel asymmetry and symmetry values) for one or more periodic structures within the target. At 1610, a slope of a fit of data of asymmetry A against symmetry S. At 1620, the slope of the fit of the metrology target measurement recipe is compared with the slope of the fit of another, different metrology target measurement recipe, which is previously or subsequently obtained. At 1630, which of the metrology target measurement recipes has a better slope of the fit is determined. For example, a metrology target measurement recipe with a slope closer to, or equal to, 0 indicates that overlay or similar asymmetry-based measurements made from measurements of adjacent gratings will be insensitive to variations in stack difference (grating imbalance GI). This slope therefore is a prediction of performance which can be used to distinguish a better metrology target measurement recipe from another metrology target measurement recipe with a slope further from 0. At 1640, optionally one or more further metrology target measurement recipes are evaluated in accordance with 1600-1630. At 1650, one or more desirable metrology target measurement recipes are output based on the analysis of the slope of the fit.

FIG. 17 is a flowchart illustrating a process in which a metrology target is used to monitor performance, and as a basis for controlling metrology, design and/or production processes. In step 1700, substrates are processed to produce product features and one or more metrology targets, for example targets of the type illustrated in FIG. 4. At step 1710, values of a patterning process performance parameter (e.g., overlay) are measured and calculated using, e.g., the method of FIG. 6. Optionally, based on GI sensitivity information and a measured stack difference, corrected values of the patterning process performance parameter are calculated in accordance with a method described above with reference to FIG. 12 above. At step 1720, the determined patterning process parameter value may be used (together with other information as may be available), to update, change, etc. a metrology target measurement recipe. Alternatively or in addition, a prediction of performance of the measurement method itself, for example a GI sensitivity measure determined by a method described above, is used to determine a better metrology target measurement recipe from among a number of possible recipes. The updated, changed, etc. metrology target measurement recipe can be used for subsequent measurement of the patterning process parameter (e.g., for measurement of the patterning process parameter on a subsequently processed substrate). In this way, the calculated patterning process parameter can be improved in accuracy. The updating process can be automated if desired. In step 1730, the patterning process parameter value can be used to control, modify, design, etc. a lithographic patterning step/apparatus and/or other process step/apparatus in the patterning process for, e.g., re-work and/or for processing of further substrates. Again this updating can be automated if desired.

One or more of the following are features can be made possible by the concepts described herein: stack difference (GI) measurements together with GI sensitivity for correction of overlay error measurements in inline measurement can be used to obtain more accurate overlay measurements; process-robust metrology target measurement recipes can be identified using GI sensitivity; and/or a desirable metrology target measurement recipe can be determined from calculated stack difference (GI).

The methods described herein may require no new reticle design, no change in metrology design and/or no increase in metrology target real-estate. The methods are also capable of broader application, for example, the stack difference can be used for process stability monitoring.

While the embodiments have focused on $+1^{st}$ and $-1^{st}$ diffraction order radiation, other diffraction orders of radiation may be considered and processed.

While the embodiments disclosed above are described in terms of diffraction based overlay measurements (e.g., measurements made using the second measurement branch of the apparatus shown in FIG. 3A), in principle the same models can be used for pupil based overlay measurements (e.g., measurements made using the first measurement branch of the apparatus shown in FIG. 3A). Consequently, it should be appreciated that the concepts described herein may be applicable to diffraction based overlay measurements and pupil based overlay measurements. Depending on the implementation, for example, it may be a solution to measure the GI sensitivity in the field image branch (sensor 23) and then apply the learning to predict GI sensitivity for measurements made using the pupil image sensor 19. In other words, it may be considered to obtain the prediction of performance of a measurement method using a sensor different to the sensor used in the measurement method itself.

While embodiments of the metrology target described herein have mostly been described in the terms of overlay measurement, embodiments of the metrology target described herein may be used to measure one or more additional or alternative patterning process parameters. For example, appropriately designed metrology targets may be used to measure exposure dose variation, measure exposure focus/defocus, measure CD, etc., all based on asymmetry difference between pairs of biased gratings. Further, the description here may also apply, with modifications as appropriate, to, e.g., substrate and/or patterning device alignment in a lithographic apparatus using an alignment mark. Similarly, the appropriate recipe for the alignment measurement may be determined.

While the target structures described above are metrology targets specifically designed and formed for the purposes of measurement, in other embodiments, properties may be measured on targets which are functional parts of devices formed on the substrate. Many devices have regular, periodic structures akin to a grating. The term "target", "grating" or "periodic structure" of a target as used herein does not require that the applicable structure has been provided specifically for the measurement being performed. Further, pitch P of the metrology target is close to the resolution limit of the optical system of the measurement tool, but may be much larger than the dimension of typical product features made by a patterning process in the target portions C. In practice the features and/or spaces of the gratings may be made to include smaller structures similar in dimension to the product features.

In association with the physical structures of the targets as realized on substrates and patterning devices, an embodiment may include a computer program containing one or more sequences of machine-readable instructions and/or functional data describing the target design, describing a method of designing a target for a substrate, describing a method of producing a target on a substrate, describing a method of measuring a target on a substrate and/or describing a method of analyzing a measurement to obtain information about a patterning process. This computer program may be executed for example within unit PU in the apparatus of FIG. 3 and/or the control unit LACU of FIG. 2. There may also be provided a data storage medium (e.g., semiconductor memory, magnetic or optical disk) having such a computer program stored therein. Where an existing inspection apparatus, for example of the type shown in FIG. 3, is already in production and/or in use, an embodiment can be implemented by the provision of an updated computer program product for causing a processor to perform one or more of the methods described herein (e.g., calculate overlay error as described herein). The program may optionally be arranged to control the optical system, substrate support and the like to perform a method of measuring a parameter of the patterning process on a suitable plurality of targets (e.g., to measure for determining stack difference and/or structural asymmetry on a suitable plurality of targets and/or to determine overlay error). The program can update a parameter of the patterning process and/or of the metrology recipe, for measurement of further substrates. The program may be arranged to control (directly or indirectly) the lithographic apparatus for the patterning and processing of further substrates.

An embodiment of the invention may take the form of a computer program containing one or more sequences of machine-readable instructions describing a method as disclosed herein, or a data storage medium (e.g. semiconductor memory, magnetic or optical disk) having such a computer program stored therein. Further, the machine readable instruction may be embodied in two or more computer programs. The two or more computer programs may be stored on one or more different memories and/or data storage media.

One or more aspects disclosed herein may be embedded in a control system. Any control system described herein may each or in combination be operable when the one or more computer programs are read by one or more computer processors located within at least one component of an apparatus. The control systems may each or in combination have any suitable configuration for receiving, processing, and sending signals. One or more processors are configured to communicate with the at least one of the control systems. For example, each control system may include one or more processors for executing the computer programs that include machine-readable instructions for the methods described above. The control systems may include data storage medium for storing such computer programs, and/or hardware to receive such medium. So the control system(s) may operate according the machine readable instructions of one or more computer programs.

Although specific reference may have been made above to the use of embodiments in the context of optical lithography, it will be appreciated that embodiments of the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of predicting performance of a measurement method, the measurement method being based on asymmetry in a diffraction spectrum of periodic features within one or more target structures formed by a lithographic process, the method of predicting performance including the steps:
   (a) forming first and second images of the target structure using symmetrically opposite portions of the diffraction spectrum of radiation diffracted by the target structure;
   (b) from the first and second images, deriving multiple local measurements of symmetry and asymmetry of intensity between opposite portions of the diffraction spectrum, each local measurement of symmetry and asymmetry corresponding to a particular location on the target structure; and
   (c) based on a statistical analysis of the local measurements of symmetry and asymmetry values, determining a prediction of performance for the measurement method.

2. The method of claim 1, wherein steps (a) to (c) are repeated using different measurement conditions to obtain predictions of performance of the measurement method under different measurement conditions.

3. The method of claim 2, further comprising a step (d) performing the measurement method to obtain a measurement of a property of the same or a similar target structure, wherein in step (d) the measurement method is performed using measurement conditions selected by comparing the obtained predictions of performance.

4. The method of claim 1, further comprising a step (d) performing the measurement method to obtain a measurement of a property of the same or a similar target structure.

5. The method of claim 3, further comprising a step (e) reporting the measurement of the property of the target structure together with a prediction of performance of the measurement method.

6. The method of claim 3, wherein step (d) further comprises applying a correction to the measurement of the property, using the prediction of performance obtained in step (c).

7. The method of claim 6, wherein the correction is based on the prediction of performance obtained in step (c) and a measurement of an additional property of the same or similar target structure.

8. The method of claim 7, wherein in step (d) the measurement of the property of the target is based on differences in asymmetry observed between two or more target structures within the same or similar target structure and the measurement of an additional property is based on differences in symmetry observed between the two or more periodic structures.

9. The method of claim 4, further comprising a step (e) reporting the measurement of the property of the target structure together with a prediction of performance of the measurement method.

10. The method of claim 4, wherein the step (d) is repeated for target structures fanned by lithography on a plurality of substrates and the steps (a) to (c) are repeated at least for each substrate.

11. The method of claim 10, wherein the step (d) is repeated for a plurality of target structures formed by lithography on one substrate and the steps (a) to (c) are repeated for multiple target structures on the same substrate.

12. The method of claim 4, wherein in the step (d) the measurement method is based on one or more global measurements of asymmetry of intensity between opposite portions of the diffraction spectrum, each global measurement asymmetry corresponding to a region of interest in each of the first and second images, the region of interest extending over a larger area of the target structure than the local measurements of symmetry and asymmetry.

13. The method of claim 4, wherein in the step (d) the measurement method is based on global measurements of asymmetry for two or more target structures whose asymmetries differ from one another by a programmed bias amount.

14. The method of claim 13, wherein in steps (a) to (c) the prediction of performance of the measurement method is based on local measurements made on one such target structure.

15. The method of claim 13, wherein in steps (a) to (c) the prediction of performance of the measurement method is based on local measurements made on two or more such target structures.

16. The method 13, wherein in the step (a) the first image is captured for the two or more target structures at different locations in a common image field.

17. The method of claim 1, wherein in the step (a) the first and second images of at least one target structure are captured at different locations in a common image field.

18. The method of claim 1, wherein each local measurement is based on an individual pixel value in each of the first and second images.

19. The method of claim 1, wherein in step (c) the prediction of performance is based on a correlation between symmetry values and asymmetry values over a set of local measurements.

20. The method of claim 19, wherein in step (c) the prediction of performance is based on a gradient of a dependency between asymmetry and symmetry in the local measurements, a lower gradient indicating a greater sensitivity to difference between symmetry in different target structures.

21. A non-transitory computer program product comprising machine-readable instructions for causing a processor to perform a measurement method based on asymmetry in a diffraction spectrum of periodic features within one or more target structures formed by a lithographic process and to perform operations comprising:
    (a) forming first and second images of a target structure using symmetrically opposite portions of the diffraction spectrum of radiation diffracted by the target structure;
    (b) from the first and second images, deriving multiple local measurements of symmetry and asymmetry of intensity between opposite portions of the diffraction spectrum, each local measurement of symmetry and asymmetry corresponding to a particular location on the target structure; and
    (c) based on a statistical analysis of the local measurements of symmetry and asymmetry values, determining a prediction of performance for the measurement method.

22. A system comprising:
an inspection apparatus configured to provide a beam of radiation on a target structure on a substrate and to detect radiation diffracted by the targets to determine a parameter of a patterning process; and
a non-transitory computer program product comprising machine-readable instructions configured to cause a processor to measure, based on asymmetry in a diffraction spectrum of periodic features within one or more target structures formed by a lithographic process, such that the processor is configure to:
    (a) form first and second images of a target structure using symmetrically opposite portions of the diffraction spectrum of radiation diffracted by the target structure;
    (b) from the first and second images, derive multiple local measurements of symmetry and asymmetry of intensity between opposite portions of the diffraction spectrum, each local measurement of symmetry and asymmetry corresponding to a particular location on the target structure; and
    (c) based on a statistical analysis of the local measurements of symmetry and asymmetry values, determine a prediction of performance for the measurement method.

23. The system of claim 22, further comprising a lithographic apparatus comprising a support structure configured to hold a patterning device to modulate a radiation beam and a projection optical system arranged to project the modulated radiation beam onto a radiation-sensitive substrate.

* * * * *

UNITED STATES PATENT AND TRADEMARK OFFICE
CERTIFICATE OF CORRECTION

PATENT NO.        : 10,289,008 B2
APPLICATION NO.   : 15/834763
DATED             : May 14, 2019
INVENTOR(S)       : Martin Jacobus Johan Jak Page 1 of 1

It is certified that error appears in the above-identified patent and that said Letters Patent is hereby corrected as shown below:

In the Claims

In Column 34, Line 63, please replace "target structures fanned" with --target structures formed--.

In Column 36, Line 27, please replace "is configure to:" with --is configured to:--.

Signed and Sealed this
Tenth Day of September, 2019

Andrei Iancu
*Director of the United States Patent and Trademark Office*